(12) United States Patent
Levine et al.

(10) Patent No.: US 9,569,986 B2
(45) Date of Patent: Feb. 14, 2017

(54) SYSTEM AND METHOD FOR GATHERING AND ANALYZING BIOMETRIC USER FEEDBACK FOR USE IN SOCIAL MEDIA AND ADVERTISING APPLICATIONS

(71) Applicant: The Nielsen Company (US), LLC, New York, NY (US)

(72) Inventors: Brian Levine, Needham, MA (US); Carl Marci, Boston, MA (US); Ravi Kanth V. Kothuri, Nashua, NH (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

(21) Appl. No.: 13/779,497

(22) Filed: Feb. 27, 2013

(65) Prior Publication Data
US 2013/0280682 A1    Oct. 24, 2013

Related U.S. Application Data

(60) Provisional application No. 61/603,528, filed on Feb. 27, 2012.

(51) Int. Cl.
*G09B 19/00*        (2006.01)
*G09B 25/00*        (2006.01)
*G06N 99/00*        (2010.01)
*G06Q 50/00*        (2012.01)

(52) U.S. Cl.
CPC ............ *G09B 25/00* (2013.01); *G06N 99/005* (2013.01); *G06Q 50/01* (2013.01); *G09B 19/00* (2013.01)

(58) Field of Classification Search
USPC ........................................................ 434/236
See application file for complete search history.

(56) References Cited

U.S. PATENT DOCUMENTS

| | | | |
|---|---|---|---|
| 2,549,836 A | 4/1951 | McIntyre et al. |
| 3,490,439 A | 1/1970 | Rolston |
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |

(Continued)

FOREIGN PATENT DOCUMENTS

| | | |
|---|---|---|
| EP | 1087618 | 12/2003 |
| EP | 1609418 | 12/2005 |

(Continued)

OTHER PUBLICATIONS

U.S. Appl. No. 12/749,376, filed Mar. 29, 2010.

(Continued)

*Primary Examiner* — James Hull
(74) *Attorney, Agent, or Firm* — Hanley, Flight & Zimmerman, LLC

(57) ABSTRACT

A system and method for measuring biologically and behaviorally based responses to social media, locations, or experiences and providing instant and continuous feedback in response thereto. The system and method of the invention is capable of monitoring stress levels and well-being and may be implemented using a cloud-based infrastructure for remote monitoring.

23 Claims, 9 Drawing Sheets

(56) References Cited

U.S. PATENT DOCUMENTS

| | | |
|---|---|---|
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,870,579 A | 9/1989 | Hey |
| 4,885,687 A | 12/1989 | Carey |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. ............ 364/419.2 |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,331,544 A | 7/1994 | Lu et al. |
| 5,339,826 A | 8/1994 | Schmidt et al. |
| 5,345,281 A | 9/1994 | Taboada et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,410,609 A | 4/1995 | Kado et al. |
| 5,436,830 A | 7/1995 | Zaltman |
| 5,447,166 A | 9/1995 | Gevins |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,617,855 A | 4/1997 | Waletzky et al. |
| 5,655,534 A | 8/1997 | Ilmoniemi |
| 5,676,138 A | 10/1997 | Zawlinski |
| 5,676,148 A | 10/1997 | Koo et al. |
| 5,687,322 A | 11/1997 | Deaton et al. |
| 5,720,619 A | 2/1998 | Fisslinger |
| 5,724,987 A | 3/1998 | Gevins et al. |
| 5,729,205 A | 3/1998 | Kwon |
| 5,736,986 A | 4/1998 | Sever, Jr. |
| 5,740,035 A | 4/1998 | Cohen et al. |
| 5,762,611 A | 6/1998 | Lewis et al. |
| 5,771,897 A | 6/1998 | Zufrin |
| 5,774,591 A | 6/1998 | Black et al. |
| 5,787,187 A | 7/1998 | Bouchard et al. |
| 5,800,351 A | 9/1998 | Mann |
| 5,802,208 A | 9/1998 | Podilchuk et al. |
| 5,802,220 A | 9/1998 | Black et al. |
| 5,812,642 A | 9/1998 | Leroy |
| 5,817,029 A | 10/1998 | Gevins et al. |
| 5,842,199 A | 11/1998 | Miller et al. |
| 5,848,399 A | 12/1998 | Burke |
| 5,892,566 A | 4/1999 | Bullwinkel |
| 5,945,863 A | 8/1999 | Coy |
| 5,961,332 A | 10/1999 | Joao |
| 5,974,262 A * | 10/1999 | Fuller et al. .................... 710/18 |
| 5,983,129 A | 11/1999 | Cowan et al. |
| 5,995,868 A | 11/1999 | Dorfmeister et al. |
| 6,001,065 A | 12/1999 | DeVito |
| 6,021,346 A | 2/2000 | Ryu et al. |
| 6,032,129 A | 2/2000 | Greef et al. |
| 6,052,619 A | 4/2000 | John |
| 6,088,040 A | 7/2000 | Oda et al. |
| 6,099,319 A | 8/2000 | Zaltman et al. .............. 434/236 |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,173,260 B1 | 1/2001 | Slaney |
| 6,175,753 B1 | 1/2001 | Menkes et al. |
| 6,182,113 B1 | 1/2001 | Narayanaswami |
| 6,190,314 B1 * | 2/2001 | Ark et al. ..................... 600/300 |
| 6,212,502 B1 | 4/2001 | Ball et al. |
| 6,228,038 B1 | 5/2001 | Claessens |
| 6,236,885 B1 | 5/2001 | Hunter et al. |
| 6,236,975 B1 | 5/2001 | Boe et al. |
| 6,254,536 B1 | 7/2001 | DeVito |
| 6,280,198 B1 | 8/2001 | Calhoun et al. |
| 6,286,005 B1 | 9/2001 | Cannon |
| 6,289,234 B1 | 9/2001 | Mueller |
| 6,292,688 B1 | 9/2001 | Patton .......................... 600/544 |
| 6,299,308 B1 | 10/2001 | Voronka et al. |
| 6,301,493 B1 | 10/2001 | Marro et al. |
| 6,315,569 B1 | 11/2001 | Zaltman ....................... 434/236 |
| 6,330,470 B1 | 12/2001 | Tucker et al. |
| 6,334,778 B1 | 1/2002 | Brown |
| 6,358,201 B1 | 3/2002 | Childre et al. |
| 6,370,513 B1 | 4/2002 | Kolawa et al. |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill .............................. 600/300 |
| 6,434,419 B1 | 8/2002 | Gevins et al. |
| 6,435,878 B1 | 8/2002 | Reynolds et al. |
| 6,453,194 B1 | 9/2002 | Hill |
| 6,453,241 B1 | 9/2002 | Bassett, Jr. et al. |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,678,685 B2 | 1/2004 | McGill et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopenathan et al. |
| 6,788,882 B1 | 9/2004 | Geer et al. |
| 6,792,304 B1 | 9/2004 | Silberstein |
| 6,842,877 B2 | 1/2005 | Robarts et al. |
| 6,850,252 B1 | 2/2005 | Hoffberg |
| 6,852,875 B2 | 2/2005 | Prakash |
| 6,888,457 B2 | 5/2005 | Wilkinson et al. |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |

(56) References Cited

U.S. PATENT DOCUMENTS

| | | |
|---|---|---|
| 6,993,380 B1 | 1/2006 | Modarres |
| 7,020,508 B2 * | 3/2006 | Stivoric et al. ............... 600/390 |
| 7,043,056 B2 | 5/2006 | Edwards et al. |
| 7,113,916 B1 | 9/2006 | Hill |
| 7,120,880 B1 | 10/2006 | Dryer et al. |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,246,081 B2 | 7/2007 | Hill |
| 7,249,708 B2 | 7/2007 | McConnell et al. |
| 7,269,590 B2 | 9/2007 | Hull et al. |
| 7,272,982 B2 | 9/2007 | Neuhauser et al. |
| 7,286,871 B2 | 10/2007 | Cohen |
| 7,340,060 B2 | 3/2008 | Tomkins et al. |
| 7,359,894 B1 | 4/2008 | Liebman et al. |
| 7,391,835 B1 | 6/2008 | Gross et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,483,844 B2 | 1/2009 | Takakura et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,630,757 B2 | 12/2009 | Dorfmeister et al. |
| 7,636,456 B2 | 12/2009 | Collins et al. |
| 7,650,793 B2 | 1/2010 | Jensen et al. |
| 7,657,523 B2 | 2/2010 | Ebanks |
| 7,689,272 B2 | 3/2010 | Farwell |
| 7,697,979 B2 | 4/2010 | Martinerie et al. |
| 7,698,238 B2 * | 4/2010 | Barletta et al. ............... 706/16 |
| 7,720,351 B2 | 5/2010 | Levitan |
| 7,729,755 B2 | 6/2010 | Laken |
| 7,797,186 B2 | 9/2010 | Dybus |
| 7,809,420 B2 | 10/2010 | Hannula et al. |
| 7,840,248 B2 | 11/2010 | Fuchs et al. |
| 7,840,250 B2 | 11/2010 | Tucker |
| 7,844,484 B2 | 11/2010 | Arnett et al. |
| 7,865,394 B1 | 1/2011 | Calloway |
| 7,892,764 B2 | 2/2011 | Xiong et al. |
| 7,895,075 B2 | 2/2011 | Gettys et al. |
| 7,908,133 B2 | 3/2011 | Neuhauser |
| 7,917,366 B1 | 3/2011 | Levanon et al. |
| 7,930,199 B1 | 4/2011 | Hill ............... 705/7.29 |
| 7,946,974 B2 | 5/2011 | Lordereau |
| 7,962,315 B2 | 6/2011 | Jensen et al. |
| 7,974,889 B2 | 7/2011 | Raimbeault |
| 7,988,557 B2 | 8/2011 | Soderlund |
| 8,014,847 B2 | 9/2011 | Shastri et al. |
| 8,027,518 B2 | 9/2011 | Baker et al. |
| 8,055,722 B2 | 11/2011 | Hille |
| 8,060,795 B2 | 11/2011 | Bakekolo et al. |
| 8,065,203 B1 | 11/2011 | Chien et al. |
| 8,069,125 B2 | 11/2011 | Jung et al. |
| 8,073,707 B2 * | 12/2011 | Teller et al. ............... 705/2 |
| 8,079,054 B1 | 12/2011 | Dhawan et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,103,328 B2 | 1/2012 | Turner et al. |
| 8,135,606 B2 | 3/2012 | Dupree |
| 8,151,298 B2 | 4/2012 | Begeja et al. |
| 8,165,916 B2 | 4/2012 | Hoffberg et al. |
| 8,179,604 B1 | 5/2012 | Prada Gomez et al. |
| 8,200,775 B2 | 6/2012 | Moore |
| 8,209,224 B2 | 6/2012 | Pradeep et al. |
| 8,229,469 B2 | 7/2012 | Zhang et al. |
| 8,235,725 B1 | 8/2012 | Hill |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,296,172 B2 | 10/2012 | Marci et al. |
| 8,300,526 B2 | 10/2012 | Saito et al. |
| 8,326,002 B2 | 12/2012 | Hill |
| 8,327,395 B2 | 12/2012 | Lee |
| 8,332,883 B2 | 12/2012 | Lee |
| 8,335,715 B2 | 12/2012 | Pradeep et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,442,429 B2 | 5/2013 | Hawit |
| 8,467,133 B2 | 6/2013 | Miller |
| 8,473,345 B2 | 6/2013 | Pradeep et al. |
| 8,477,425 B2 | 7/2013 | Border et al. |
| 8,484,081 B2 | 7/2013 | Pradeep et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |
| 8,543,446 B2 | 9/2013 | Richardson et al. |
| 8,548,852 B2 | 10/2013 | Pradeep et al. |
| 8,560,530 B2 | 10/2013 | Krichman et al. |
| 8,561,095 B2 * | 10/2013 | Dimitrova et al. ............ 725/10 |
| 8,600,100 B2 | 12/2013 | Hill |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 8,684,742 B2 | 4/2014 | Siefert |
| 8,700,009 B2 * | 4/2014 | Quy ............... 455/414.1 |
| 8,764,652 B2 | 7/2014 | Lee et al. |
| 8,788,372 B2 | 7/2014 | Kettner et al. |
| 8,793,715 B1 | 7/2014 | Weitzenfeld et al. |
| 8,793,727 B2 * | 7/2014 | Serdiuk ............... 725/36 |
| 8,856,235 B2 | 10/2014 | Zhou et al. |
| 8,874,727 B2 | 10/2014 | Swahar |
| 2001/0013009 A1 | 8/2001 | Greening et al. |
| 2001/0020236 A1 | 9/2001 | Cannon |
| 2001/0029468 A1 | 10/2001 | Yamaguchi et al. |
| 2001/0056225 A1 | 12/2001 | DeVito |
| 2002/0053076 A1 | 5/2002 | Landesmann |
| 2002/0055857 A1 | 5/2002 | Mault |
| 2002/0056124 A1 | 5/2002 | Hay |
| 2002/0059577 A1 | 5/2002 | Lu et al. |
| 2002/0065826 A1 | 5/2002 | Bell et al. |
| 2002/0072952 A1 | 6/2002 | Hamzy et al. |
| 2002/0077534 A1 | 6/2002 | DuRousseau |
| 2002/0082902 A1 | 6/2002 | Ando et al. |
| 2002/0103429 A1 | 8/2002 | deCharms |
| 2002/0143627 A1 | 10/2002 | Barsade et al. |
| 2002/0155878 A1 | 10/2002 | Lert, Jr. et al. |
| 2002/0156842 A1 | 10/2002 | Signes et al. |
| 2002/0169665 A1 | 11/2002 | Hughes et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1 | 1/2003 | Gevins et al. |
| 2003/0036955 A1 | 2/2003 | Tanaka et al. |
| 2003/0037333 A1 | 2/2003 | Ghashghai et al. |
| 2003/0044050 A1 * | 3/2003 | Clark ............... G06F 21/32 382/115 |
| 2003/0059750 A1 | 3/2003 | Bindler et al. |
| 2003/0063222 A1 * | 4/2003 | Creed et al. ............... 348/687 |
| 2003/0065524 A1 | 4/2003 | Giacchetti et al. |
| 2003/0073921 A1 | 4/2003 | Sohmer et al. |
| 2003/0081834 A1 | 5/2003 | Philomin et al. |
| 2003/0093792 A1 | 5/2003 | Labeeb et al. |
| 2003/0100998 A2 | 5/2003 | Brunner et al. |
| 2003/0104865 A1 | 6/2003 | Itkis et al. |
| 2003/0149344 A1 | 8/2003 | Nizan |
| 2003/0165270 A1 | 9/2003 | Endrikhovski et al. |

(56) References Cited

U.S. PATENT DOCUMENTS

| | | |
|---|---|---|
| 2003/0177488 A1 | 9/2003 | Smith et al. |
| 2003/0204412 A1 | 10/2003 | Brier |
| 2003/0208754 A1 | 11/2003 | Sridhar et al. |
| 2003/0233278 A1 | 12/2003 | Marshall |
| 2004/0001616 A1 | 1/2004 | Gutta et al. |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0055448 A1* | 3/2004 | Byon ............................ 84/626 |
| 2004/0068431 A1 | 4/2004 | Smith et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0133081 A1 | 7/2004 | Teller et al. |
| 2004/0187167 A1 | 9/2004 | Maguire et al. |
| 2004/0193068 A1 | 9/2004 | Burton et al. |
| 2004/0210159 A1 | 10/2004 | Kibar |
| 2004/0219184 A1 | 11/2004 | Brown et al. |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0041951 A1 | 2/2005 | Inoue et al. |
| 2005/0060312 A1 | 3/2005 | Curtiss et al. |
| 2005/0062637 A1 | 3/2005 | El Zabadani et al. |
| 2005/0071462 A1 | 3/2005 | Bodin et al. |
| 2005/0071865 A1 | 3/2005 | Martins |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0113649 A1 | 5/2005 | Bergantino |
| 2005/0143629 A1 | 6/2005 | Farwell |
| 2005/0154290 A1 | 7/2005 | Langleben |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0216243 A1 | 9/2005 | Graham et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0256905 A1 | 11/2005 | Gruhl et al. |
| 2005/0267798 A1 | 12/2005 | Panara |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0035707 A1 | 2/2006 | Nguyen et al. |
| 2006/0041548 A1 | 2/2006 | Parsons et al. |
| 2006/0042483 A1 | 3/2006 | Work et al. |
| 2006/0053110 A1 | 3/2006 | McDonald et al. |
| 2006/0069663 A1 | 3/2006 | Adar et al. |
| 2006/0075003 A1 | 4/2006 | Adams et al. |
| 2006/0093998 A1 | 5/2006 | Vertegaal |
| 2006/0111044 A1 | 5/2006 | Keller |
| 2006/0111644 A1 | 5/2006 | Guttag et al. |
| 2006/0129458 A1 | 6/2006 | Maggio ............................ 705/14 |
| 2006/0149337 A1 | 7/2006 | John |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0176289 A1 | 8/2006 | Horn |
| 2006/0190822 A1 | 8/2006 | Basson et al. |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0259371 A1 | 11/2006 | Perrier et al. |
| 2006/0293921 A1 | 12/2006 | McCarthy et al. |
| 2007/0016096 A1 | 1/2007 | McNabb |
| 2007/0038516 A1 | 2/2007 | Apple et al. |
| 2007/0048707 A1 | 3/2007 | Caamano et al. |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0061720 A1 | 3/2007 | Kriger |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078700 A1 | 4/2007 | Lenzmann et al. |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0112460 A1 | 5/2007 | Kiselik |
| 2007/0135727 A1 | 6/2007 | Virtanen et al. |
| 2007/0135728 A1 | 6/2007 | Snyder et al. |
| 2007/0150916 A1 | 6/2007 | Begole et al. |
| 2007/0198510 A1 | 8/2007 | Ebanks |
| 2007/0214121 A1 | 9/2007 | Ebanks |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0239713 A1 | 10/2007 | Leblang |
| 2007/0250846 A1 | 10/2007 | Swix et al. |
| 2007/0250901 A1 | 10/2007 | McIntire et al. |
| 2007/0265507 A1 | 11/2007 | de Lemos |
| 2007/0282566 A1 | 12/2007 | Whitlow et al. |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0004940 A1 | 1/2008 | Rolleston Phillips |
| 2008/0010110 A1 | 1/2008 | Neuhauser et al. |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091463 A1 | 4/2008 | Shakamuri |
| 2008/0091512 A1 | 4/2008 | Marci et al. |
| 2008/0097854 A1 | 4/2008 | Young ............................ 705/14 |
| 2008/0109840 A1 | 5/2008 | Walter et al. |
| 2008/0125110 A1 | 5/2008 | Ritter |
| 2008/0133724 A1 | 6/2008 | Clark |
| 2008/0147488 A1 | 6/2008 | Tunick et al. |
| 2008/0147742 A1 | 6/2008 | Allen |
| 2008/0152300 A1 | 6/2008 | Knee et al. |
| 2008/0162182 A1 | 7/2008 | Cazares et al. |
| 2008/0195471 A1 | 8/2008 | Dube et al. |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0249865 A1 | 10/2008 | Angell et al. |
| 2008/0255949 A1 | 10/2008 | Genco et al. ............... 705/14 |
| 2008/0287821 A1 | 11/2008 | Jung |
| 2008/0295126 A1 | 11/2008 | Lee et al. |
| 2008/0306398 A1 | 12/2008 | Uchiyama et al. |
| 2009/0018996 A1 | 1/2009 | Hunt et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0024747 A1 | 1/2009 | Moses et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |

(56) References Cited

U.S. PATENT DOCUMENTS

| | | |
|---|---|---|
| 2009/0030762 A1 | 1/2009 | Lee et al. |
| 2009/0030780 A1 | 1/2009 | York et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0066722 A1 | 3/2009 | Kriger |
| 2009/0069652 A1 | 3/2009 | Lee et al. |
| 2009/0070219 A1 | 3/2009 | D'Angelo et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1* | 4/2009 | Lee et al. ............... 600/301 |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0099873 A1 | 4/2009 | Kurple |
| 2009/0112077 A1 | 4/2009 | Nguyen et al. |
| 2009/0112117 A1 | 4/2009 | Rewari |
| 2009/0119154 A1 | 5/2009 | Jung et al. |
| 2009/0131764 A1 | 5/2009 | Lee et al. ............... 600/301 |
| 2009/0132441 A1 | 5/2009 | Muller et al. |
| 2009/0133047 A1 | 5/2009 | Lee et al. |
| 2009/0138356 A1 | 5/2009 | Pomplun |
| 2009/0144780 A1 | 6/2009 | Toebes et al. |
| 2009/0150919 A1 | 6/2009 | Lee et al. |
| 2009/0150920 A1 | 6/2009 | Jones |
| 2009/0153328 A1 | 6/2009 | Otani et al. |
| 2009/0156907 A1 | 6/2009 | Jung et al. |
| 2009/0156955 A1 | 6/2009 | Jung et al. |
| 2009/0158308 A1 | 6/2009 | Weitzenfeld et al. |
| 2009/0163777 A1 | 6/2009 | Jung |
| 2009/0164132 A1 | 6/2009 | Jung et al. |
| 2009/0171164 A1 | 7/2009 | Jung et al. |
| 2009/0187467 A1 | 7/2009 | Fang et al. |
| 2009/0195392 A1 | 8/2009 | Zalewski |
| 2009/0214060 A1 | 8/2009 | Chuang et al. |
| 2009/0216611 A1 | 8/2009 | Leonard et al. |
| 2009/0221928 A1 | 9/2009 | Einav et al. |
| 2009/0248484 A1 | 10/2009 | Surendran et al. |
| 2009/0248496 A1 | 10/2009 | Hueter et al. |
| 2009/0248594 A1 | 10/2009 | Castleman et al. |
| 2009/0253996 A1 | 10/2009 | Lee et al. |
| 2009/0259137 A1 | 10/2009 | Delic et al. |
| 2009/0259509 A1 | 10/2009 | Landvater |
| 2009/0287108 A1 | 11/2009 | Levy |
| 2009/0292587 A1 | 11/2009 | Fitzgerald |
| 2009/0300672 A1 | 12/2009 | Van Gulik |
| 2009/0305006 A1 | 12/2009 | Steffen |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0327907 A1 | 12/2009 | Estrada et al. |
| 2009/0328089 A1 | 12/2009 | Pradeep et al. |
| 2010/0004977 A1* | 1/2010 | Marci et al. ............... 705/10 |
| 2010/0022821 A1 | 1/2010 | Dubi et al. |
| 2010/0039618 A1 | 2/2010 | De Lemos |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0094702 A1 | 4/2010 | Silberstein |
| 2010/0094869 A1 | 4/2010 | Ebanks |
| 2010/0121716 A1 | 5/2010 | Golan |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0153175 A1 | 6/2010 | Pearson et al. |
| 2010/0169153 A1 | 7/2010 | Hwacinski et al. |
| 2010/0169162 A1 | 7/2010 | Anderson et al. |
| 2010/0179881 A1 | 7/2010 | Wiederstein |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0211439 A1 | 8/2010 | Marci et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0223094 A1 | 9/2010 | Cumming et al. |
| 2010/0228604 A1 | 9/2010 | Desai et al. |
| 2010/0228614 A1 | 9/2010 | Zhang et al. |
| 2010/0234752 A1 | 9/2010 | Sullivan et al. |
| 2010/0241580 A1 | 9/2010 | Schleier-Smith |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250458 A1 | 9/2010 | Ho |
| 2010/0257023 A1 | 10/2010 | Kendall et al. |
| 2010/0257052 A1 | 10/2010 | Zito et al. |
| 2010/0262477 A1 | 10/2010 | Hillerbrand et al. |
| 2010/0263005 A1 | 10/2010 | White |
| 2010/0268540 A1 | 10/2010 | Arshi et al. |
| 2010/0268573 A1 | 10/2010 | Jain et al. |
| 2010/0268720 A1 | 10/2010 | Spivack et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0287152 A1 | 11/2010 | Hauser |
| 2010/0292998 A1 | 11/2010 | Bodlaender et al. |
| 2010/0306120 A1 | 12/2010 | Ciptawilangga |
| 2010/0317988 A1 | 12/2010 | Terada et al. |
| 2010/0318507 A1 | 12/2010 | Grant et al. |
| 2010/0325660 A1 | 12/2010 | Holden |
| 2010/0331661 A1 | 12/2010 | Nakagawa |
| 2010/0332283 A1 | 12/2010 | Ng et al. |
| 2011/0004089 A1 | 1/2011 | Chou |
| 2011/0015503 A1 | 1/2011 | Joffe et al. |
| 2011/0020778 A1* | 1/2011 | Forbes ............... 434/236 |
| 2011/0022965 A1 | 1/2011 | Lawrence et al. |
| 2011/0040155 A1* | 2/2011 | Guzak et al. ............... 600/300 |
| 2011/0040202 A1 | 2/2011 | Luo et al. |
| 2011/0043759 A1 | 2/2011 | Bushinsky |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047035 A1 | 2/2011 | Gidwani et al. |
| 2011/0047121 A1 | 2/2011 | Pradeep et al. |
| 2011/0059422 A1 | 3/2011 | Masaoka |
| 2011/0071874 A1 | 3/2011 | Schneersohn et al. |
| 2011/0076942 A1* | 3/2011 | Taveau ............... H04M 1/2745 455/41.1 |
| 2011/0084795 A1 | 4/2011 | Fukuyori |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0119130 A1 | 5/2011 | Agan et al. |
| 2011/0124977 A1* | 5/2011 | Winarski ............... 600/301 |
| 2011/0131274 A1 | 6/2011 | Hille |
| 2011/0137894 A1 | 6/2011 | Narayanan et al. |
| 2011/0144519 A1 | 6/2011 | Causevic |
| 2011/0153390 A1 | 6/2011 | Harris |
| 2011/0153391 A1 | 6/2011 | Tenbrock |
| 2011/0153414 A1 | 6/2011 | Elvekrog et al. |
| 2011/0153423 A1 | 6/2011 | Elvekrog et al. |
| 2011/0161095 A1 | 6/2011 | Line et al. |
| 2011/0161163 A1 | 6/2011 | Carlson et al. |

(56) References Cited

U.S. PATENT DOCUMENTS

| | | |
|---|---|---|
| 2011/0161790 A1 | 6/2011 | Junior et al. |
| 2011/0191142 A1 | 8/2011 | Huang |
| 2011/0208515 A1 | 8/2011 | Neuhauser |
| 2011/0213670 A1 | 9/2011 | Strutton et al. |
| 2011/0224569 A1 | 9/2011 | Isenhart et al. |
| 2011/0237923 A1 | 9/2011 | Picht et al. |
| 2011/0237971 A1 | 9/2011 | Pradeep et al. |
| 2011/0246574 A1 | 10/2011 | Lento et al. |
| 2011/0248729 A2 | 10/2011 | Mueller et al. |
| 2011/0256520 A1 | 10/2011 | Siefert |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0282880 A1 | 11/2011 | Krichman et al. |
| 2011/0296004 A1 | 12/2011 | Swahar |
| 2011/0298706 A1 | 12/2011 | Mann |
| 2011/0301431 A1 | 12/2011 | Greicius |
| 2011/0313849 A1 | 12/2011 | Brueck et al. |
| 2011/0319975 A1 | 12/2011 | Ho et al. |
| 2012/0002848 A1 | 1/2012 | Hill |
| 2012/0004899 A1 | 1/2012 | Arshi |
| 2012/0022391 A1 | 1/2012 | Leuthardt |
| 2012/0036004 A1 | 2/2012 | Pradeep et al. |
| 2012/0036005 A1 | 2/2012 | Pradeep et al. |
| 2012/0046993 A1 | 2/2012 | Hill |
| 2012/0054018 A1 | 3/2012 | Pradeep et al. |
| 2012/0072289 A1 | 3/2012 | Pradeep et al. |
| 2012/0072845 A1* | 3/2012 | John et al. ............ 715/738 |
| 2012/0072936 A1* | 3/2012 | Small et al. ............ 725/10 |
| 2012/0078065 A1 | 3/2012 | De Lemos et al. |
| 2012/0083668 A1 | 4/2012 | Pradeep et al. |
| 2012/0084139 A1 | 4/2012 | Pradeep et al. |
| 2012/0089552 A1 | 4/2012 | Chang et al. |
| 2012/0096363 A1 | 4/2012 | Barnes et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0166252 A1 | 6/2012 | Walker |
| 2012/0173701 A1 | 7/2012 | Tenbrock |
| 2012/0203363 A1 | 8/2012 | McKenna et al. |
| 2012/0203559 A1 | 8/2012 | McKenna et al. |
| 2012/0239407 A1 | 9/2012 | Jain et al. |
| 2012/0245978 A1 | 9/2012 | Crystal et al. |
| 2012/0249797 A1 | 10/2012 | Haddick et al. |
| 2012/0254909 A1 | 10/2012 | Serdiuk |
| 2012/0272256 A1 | 10/2012 | Bedi |
| 2012/0284332 A1 | 11/2012 | Pradeep et al. |
| 2012/0290637 A1 | 11/2012 | Perantatos et al. |
| 2012/0296699 A1 | 11/2012 | Richardson et al. |
| 2012/0317198 A1 | 12/2012 | Patton et al. |
| 2013/0018949 A1 | 1/2013 | Pradeep |
| 2013/0022948 A1* | 1/2013 | Angell et al. ............ 434/236 |
| 2013/0024272 A1 | 1/2013 | Pradeep et al. |
| 2013/0046577 A1 | 2/2013 | Marci et al. |
| 2013/0060125 A1 | 3/2013 | Zeman |
| 2013/0094722 A1 | 4/2013 | Hill |
| 2013/0097715 A1* | 4/2013 | Fourman ............ 726/26 |
| 2013/0121591 A1* | 5/2013 | Hill ............ G06K 9/46 382/195 |
| 2013/0124365 A1 | 5/2013 | Pradeep |
| 2013/0143185 A1* | 6/2013 | Liu et al. ............ 434/236 |
| 2013/0152506 A1 | 6/2013 | Pradeep |
| 2013/0166373 A1 | 6/2013 | Pradeep et al. |
| 2013/0183646 A1* | 7/2013 | Lusted et al. ............ 434/236 |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0268279 A1 | 10/2013 | Srinivasan et al. |
| 2013/0280682 A1 | 10/2013 | Levine et al. |
| 2013/0304540 A1 | 11/2013 | Pradeep et al. |
| 2013/0311132 A1 | 11/2013 | Tobita |
| 2013/0332259 A1 | 12/2013 | Pradeep et al. |
| 2014/0025620 A1 | 1/2014 | Greenzeiger et al. |
| 2014/0067466 A1 | 3/2014 | Xiao et al. |
| 2014/0162225 A1 | 6/2014 | Hill |
| 2014/0214335 A1 | 7/2014 | Siefert |
| 2014/0221866 A1 | 8/2014 | Quy |
| 2014/0244345 A1 | 8/2014 | Sollis et al. |
| 2014/0278914 A1 | 9/2014 | Gurumoorthy et al. |
| 2014/0350431 A1 | 11/2014 | Hagedorn |
| 2015/0186923 A1 | 7/2015 | Gurumoorthy et al. |

FOREIGN PATENT DOCUMENTS

| | | |
|---|---|---|
| GB | 1374658 | 11/1974 |
| GB | 2221759 | 2/1990 |
| JP | 2001-147944 | 5/2001 |
| JP | 2005-51654 | 2/2005 |
| JP | 2005-160805 | 6/2005 |
| JP | 2006-227994 | 8/2006 |
| JP | 2006-305334 | 11/2006 |
| JP | 2006-6355 | 7/2007 |
| KR | 2004-22399 | 7/2006 |
| WO | 95-18565 | 7/1995 |
| WO | 97-17774 | 5/1997 |
| WO | 97-40745 | 11/1997 |
| WO | 97-41673 | 11/1997 |
| WO | 02-100241 | 12/2002 |
| WO | 02-102238 | 12/2002 |
| WO | 2004-049225 | 6/2004 |
| WO | 2008-064431 | 6/2008 |
| WO | 2008-055078 | 7/2008 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-137579 | 11/2008 |
| WO | 2008-137581 | 11/2008 |
| WO | 2008-141340 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |

OTHER PUBLICATIONS

U.S. Appl. No. 12/426,259, filed Apr. 19, 2009.

U.S. Appl. No. 13/089,752, filed Apr. 19, 2011.

"ARF, AAAA and ANA Are Getting Emotional about Engagement", Presentation, pp. 1-103 (2005).

Boltz, M.G., "The cognitive processing of film and musical soundtracks", *Memory & Cognition*, 32(7):1194-1205 (2004).

Christie et al., "Autonomic specificity of discrete emotion and dimensions of affective space: a multivariate approach", *Int'l J. Psychophysiol.*, 51:143-153 (2004).

Coombes et al., "Emotion and movement: Activation of defensive circuitry alters the magnitude of a sustained muscle contraction", *Neurosci. Lett.*, 396:192-196 (2006).

Cryer et al., "Pull the plug on stress", *Harv. Bus. Rev.*, 81(7):102-107 (2003).

Demaree et al., "Predicting facial valence to negative stimuli from resting RSA: Not a function of active emotion regulation", *Cognition and Emotion*, 20(2):161-176 (2006).

Ekman et al., "Autonomic Nervous System Activity Distinguishes among Emotions", *Science*, 221(4616):1208-1210 (1983).

Elton, C., "Measuring emotion at the symphony", http://www.boston.com, pp. 1-3 (2006).

Goldberg, C., "Getting wired could help predict emotions", http://www.boston.com, pp. 1-4 (2005).

Gomez et al., "Respiratory responses associated with affective processing of film stimuli", Biol. Psychol., 68:223-235 (2005).

Hall, B.F., "A New Approach to Measuring Advertising Effectiveness", Article 1502a:1-17 (2001).

(56) References Cited

OTHER PUBLICATIONS

Hall, B.F., "Advertising as a Factor of production", *Admap*, pp. 30-32 (2003).
Hall, B.F., "Is cognitive processing the right dimension", *Admap*, pp. 37-39 (2003).
Hall, B.F., "On Measuring the Power Communications", *JAR*, pp. 1-11 (2004).
Hall, B.F., "Research and strategy: a fall from grace", *Admap*, pp. 2-4 (2003).
Hall, B.F., "Review of Casting for Big Ideas, by Andrew Jaffe", pp. 1-2 (2003).
Hall, B.F., "Why Advertisers Do It", pp. 1-5 (2003).
Hubert, et al., "Autonomic, neuroendocrine, and subjective responses to emotion-inducing film stimuli", Int'l J. Psychophysiol., 11:131-140 (1991).
Levenson et al., "Emotion and Autonomic Nervous System Activity in the Minangkabau of West Sumatra", *J. Personality Soc. Psychol.*, 62(6):972-988 (1992).
Marci et al., "The Effect of Emotional Distance on Pyschophysiologic Concordance and Perceived Empathy Between Patient and Interviewer", *Appl. Psychophysiol. Biofeedback*, 31:115-129 (2006).
McCraty et al., "Analysis of twenty-four hour heart rate variability in patients with panic disorder", Biol. Psychol., 56(2):131-150 (2001).
McCraty et al., "Electrophysiolocial Evidence of Intuition: Part 1. The Surprising Role of the Heart", J. Altern. Complement. Med., 10(1):133-143 (2004).
McCraty et al., "Electrophysiological Evidence of Intuition: Part 2. A System-Wide Process?", J. Altern. Complement. Med., 10(2\0):325-336 (2004).
McCraty et al., "Impact of a Workplace Stress Reduction Program on Blood Pressure and Emotional Health in Hypertensive Employees", *J. Altern. Complement. Med.*, 9(3):355-369 (2003).
McCraty et al., "The Effects of Different Types of Music on Mood, Tension, and Mental Clarity", *Altern. Ther. Health Med.*, 4(1):75-84 (1998).
McCraty et al., "The Effects of Emotions on Ahort-Term Power Spectrum Analysis of Heart RateVariability", *Am. J. Cardiol.*, 76(14):1089-1093 (1995).
McCraty et al., "The Impact of a New Emotional Self-Management Program on Stress, Emotions, Heart Rate Variability, DHEA and Cortisol", *Intergr. Physiol. Behav. Sci.*, 33(2):151-170 (1998).
McCraty et al., "The Impact of an Emotional Self-Management Skills Course on Psychosocial Functioning and Autonomic Recovery to Stress in Middle School Children", Integr. Physiol. Behav. Sci., 34(4):246-268 (1999).
Melillo, W., "Inside the consumer mind: What Neuroscience can tell us about marketing", http://www.answerstream.com, pp. 1-13 (2006).
Miller et al., "Influence of Specific Emotional States on Autonomic Reactivity and Pulmonary Function in Asthmatic Children", *J. Am. Acad. Child Adolescent Psychiatry*, 36(5):669-677 (1997).
Murphy et al., "The Heart Reinnervates After Transplantation", *Ann. Thorac. Surg.*, 69(6):1769-1781 (2000).
Ranii, D., "Adding Science to Gut Check", *The News & Observer*, pp. 1 (2005).
Rosenberg, K., "Emotional R.O.I.", *The Hub*, pp. 24-25 (2006).
Tiller et al., "Cardiac Coherence: A New, Noninvasive Measure of Autonomic Nervous System Order", *Altern. Ther. Health Med.*, 2(1):52-65 (1996).
"Topline: Emotional Response to Advertising", *MSW Research*, pp. 1-6 (2005).
Umetani et al., "Twenty-Four Hour Time Domain Heart Rate Variability and Heart Rate: Relations to Age and Gender Over Nine Decades", *J. Am. Coll. Cardiol.*, 31(3):593-601 (1998).
Von Leupoldt et al., "Emotions in a Body Plethysmograph", *J. Psychophysiol.*, 18(4):170-176 (2004).
Kallman, H. Effect of Blank Time on Picture Recognition. The American Journal of Psychology, vol. 97, No. 3, Autumn, 1984, pp. 399-406 [retrieved on Nov. 3, 2011]. Retrieved from the Internet: <URL: http://www.jstor.org/pss/1422527>.
Larose, Daniel T., Data Mining Methods and Models, John Wiley & Sons, Inc., 2006.
Han, Micheline Kamber Jiawei, Data Mining: Concepts and Techniques, Second Edition (The Morgan Kaufmann Series in Data Management Systems), Elsevier, Inc., 2006.
Liu, Bing, Web Data Mining: Exploring Hyperlinks, Contents, and Usage Data (Data-Centric Systems and Applications), Springer-Verlag, 2007.
Berry, Michael J.A. and Linoff, Gordon S., Data Mining Techniques: For Marketing, Sales, and Customer Relationship Management, John Wiley & Sons, Inc., 1997.
Watching Ads Is Real Science Research Companies Monitor Physiological Reactions to Commercials to Determine Their Effectiveness.: [3 Star Edition] Bruce Horovitz Los Angeles Times. Orlando Sentinel [Orlando, Fla] Sep. 1, 1991; D1, 2pgs.
Wearable feedback systems for rehabilitation Sung, Michael; Marci, Carl; Pentland, Alex. Journal of NeuroEngineering and Rehabilitation 2 (2005), 2pgs.
International Search Report dated Mar. 24, 2008 of International Patent Application No. PCT/US2007/019398.
International Search Report dated Nov. 9, 2010 of International Patent Application No. PCT/US2010/031375.
International Search Report dated Oct. 21, 2010 of International Patent Application No. PCT/US2010/029162.
International Search Report dated Nov. 22, 2011 of International Patent Application No. PCT/US2011/033050.
Non-Final Office Action dated Oct. 18, 2010 of related U.S. Appl. No. 11/850,650.
Final Office Action dated Jun. 8, 2011 of related U.S. Appl. No. 11/850,650.
Non-Final Office Action dated Dec. 13, 2011 of related U.S. Appl. No. 11/850,650.
Notice of Allowance dated Jul. 16, 2012 of related U.S. Appl. No. 11/850,650.
Non-Final Office Action dated Dec. 21, 2011 of related U.S. Appl. No. 12/749,376.
Final Office Action dated Oct. 4, 2012 of related U.S. Appl. No. 12/749,376.
Non-Final Office Action dated Apr. 1, 2013 of related U.S. Appl. No. 12/749,376.
Non-Final Office Action dated Apr. 25, 2012 of related U.S. Appl. No. 12/426,259.
Final Office Action dated Dec. 19, 2012 of related U.S. Appl. No. 12/426,259.
Non-Final Office Action dated Feb. 21, 2013 of related U.S. Appl. No. 13/657,432.
Non-Final Office Action dated Feb. 13, 2013 of related U.S. Appl. No. 13/089,752.
Australian Office Action dated Mar. 26, 2012 or corresponding Australian Patent Application No. 2007293092.
European Office Action dated Nov. 11, 2011 of corresponding European Patent Application No. 10717912.9.
European Supplementary Search Report dated Mar. 1, 2013 of corresponding European Patent Application No. 10717912.9.
European Office Action dated Mar. 14, 2013 of corresponding European Patent Application No. 10717912.9.
European Office Action dated Nov. 29, 2011 of corresponding European Patent Application No. 10717932.7.
European Search Report dated Aug. 8, 2013 of corresponding European Patent Application No. 10717932.7.
European Supplementary Search Report dated Aug. 27, 2013 of corresponding European Patent Application No. 10717932.7.
Japanese Office Action dated Apr. 23, 2012 of corresponding Japanese Patent Application No. 2009-527401.
Canadian Office Action dated Jul. 24, 2014 of related Canadian Patent Application No. 2,662,632.
Brown, M. "Should My Advertising Stimulate an Emotional Response?" 2009, available at http://www.wpp.com/~/media/sharedwpp/readingroom/marketing/millward_brown_emotional_response.pdf, 6 pages.

(56) References Cited

OTHER PUBLICATIONS

Mehta, A. et al., "Reconsidering Recall and Emotion in Advertising," Journal of Advertising Research, Mar. 2006, pp. 49-56, 8 pages.

Micu, A. C. et al., "Measurable Emotions: How Television Ads Really Work: How the Patterns of Reactions to Commercials can Demonstrate Advertising Effectiveness", Management Slant, 50(2), Jun. 2010; pp. 1-17, 18 pages.

Cheung, Kwok-Wai, et al., "Mining Customer Product Ratings for Personalized Marketing," Decision Support Systems 35, 2003, pp. 231-243, 13 pages.

Jaimes, A., Sebe, N., Multimodal Human-Computer Interaction: A Survey, Computer Vision and Image Understanding 108, Oct.-Nov. 2007, pp. 116-134, 19 pages.

Garton, L. et al., "Studying Online Social Networks", Journal of Computer-Mediated Communication, 3(1), Jun. 1997, 29 pages.

Darrow, Chester, "Psychological and psychophysiological significance of the electroencephalogram," Psychological Review (May 1947) 157-168, 12 pages.

Stamm, John, "On the Relationship between Reaction Time to Light and Latency of Blocking the Alpha Rhythm," Electroencephalography and Clinical Neurophysiology (Feb. 1952), 61-68, 8 pages.

Mizuki, Yashushi, et al., "Periodic Appearance of the Theta Rhythm in the Frontal Midline Area During Performance of a Mental Task,:" Electroencephalography and Clinical Neurophysiology (Aug. 1980), 345-351, 7 pages.

Ekman, P., Friesen, W., Measuring Facial Movement, Environmental Psychology and Nonverbal Behavior, 1(1) (Fall 1976), pp. 56-75, 20 pages.

Ekman, P., Friesen, W.V., *Facial Action Coding System: A Technique for Measurement of Facial Movement*, Consulting Psychologists Press, Palo Alto, Calif. (1978). (Book).

Ekman, P., Friesen, W., *Unmasking the Face—A Guide to Recognizing Emotions from Facial Clues*, Prentice-Hall, Inc., Englewood Cliffs, N.J. (1979). (Book).

Ekman, P., Friesen, W., Ancoli, S., Facial Signs of Emotional Experience, J. Personality & Social Psychology, 39(6) (Dec. 1980), pp. 1125-1134, 10 pages.

Izard, C. E., *The Maximally Discriminative Facial Movement Coding System*, (Rev. ed.), Instructional Resources Center, University of Delaware, Newark, Del. (1983). (Book).

Izard, C., Dougherty, L., Hembree, E., *A System for Identifying Affect Expressions by Holistic Judgments (AFFEX)*, Instructional Resources Center, University of Delaware, Newark, Del. (1983). (Book).

Jia, X., Nixon, M.S., Extending the Feature Set for Automatic Face Recognition, International Conference on Image Processing and Its Applications (Apr. 7-9, 1992), 6 pages.

Lisetti, C., Nasoz, F., Using Noninvasive Wearable Computers to Recognize Human Emotions from Physiological Signals, EURASIP J. Applied Signal Processing, 11 (Sep. 2004), pp. 1672-1687, 16 pages.

McClure, Samuel, et al., "Neural Correlates of Behavioral Preference for Culturally Familiar Drinks," Neuron (Oct. 14, 2004), 379-387, 9 pages.

Opitz, S. "Neuromarketing: An Introduction" PowerPoint Presentation (2008), available at http://www.powershow.com/view/94a7b-YzlmN/Neuromarketing_powerpoint_ppt_presentation (last accessed Oct. 14, 2015), 20 pages.

Axis Communications, "Improve your merchandising effectiveness. Get the full picture with network video" (2008), available at :http://www.axis.com/files/user_scenarios/ap_ret_merchandising_311 07_en_0803_lo.pdf, 2 pages.

Kamba, Tomonari, "The Krakatoa Chronicl—An Interactive, Personalized Newspaper on the Web," available at: http://www.w3.org/Conferences/WWW4/Papers/93/ (last accessed Nov. 2, 2015), 15 pages.

Ehrenberg et al., "Understanding Brand Performance Measures: Using Dirichlet Benchmarks," 2004, Journal of Business Research, vol. 57, pp. 1307-1325, 19 pages.

Leeflang et al., "Building Models for Marketing Decisions," 2000, Springer Science + Business Media, pp. 192-235, 482-521, 86 pages.

Bassi et al., "The Dirichlet Model: Analysis of a Market and Comparison of Estimation Procedures," 2011, Marketing Bulletin, vol. 22, Technical Note 1, pp. 1-11, 11 pages.

Bhattacharya, "Is your brand's loyalty too much, too little, or just right?: Explaining deviations in loyalty from the Dirichlet norm," 1997, International Journal of Research in Marketing, vol. 14, pp. 421-435, 15 pages.

Cohen, "Differentiated product demand analysis with a structured covariance probit: A Bayesian econometric approach," 2009, PhD dissertation, University of Connecticut, pp. 1-184, 197 pages.

Nikolaeva et al., "The Moderating Role of Consumer and Product Characteristics on the Value of Customized On-Line Recommendations," 2006, International Journal of Electronic Commerce, vol. 11, No. 2, pp. 101-123, 24 pages.

Ehrenberg, "New Brands and the Existing Market," 1991, International Journal of Market Research, vol. 33, No. 4, 10 pages.

Foxall, "The Substitutability of Brands," 1999, Managerial and Decision Economics, vol. 20, pp. 241-257, 17 pages.

Pammer, "Forecasting the Penetration of a New Product—A Bayesian Approach," 2000, Journal of Business and Economic Statistics, vol. 18, No. 4, pp. 428-435, 8 pages.

Rungie et al., "Calculation of Theoretical Brand Performance Measures from the Parameters of the Dirichlet Model," 2004, Marketing Bulletin, Massey University, 15, Technical Note 2, pp. 1-19, 20 pages.

Uncles et al., "Patterns of Buyer Behavior: Regularities, Models, and Extensions," 1995, Marketing Science, vol. 14, No. 3, pp. G71-G78, 9 pages.

Aaker et al., "Warmth in Advertising: Measurement, Impact, and Sequence Effects," Journal of Consumer Research, vol. 12, No. 4, pp. 365-381, (Mar. 1986), 18 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Bagozzi et al., "The Role of Emotions in Marketing," Journal of the Academy of Marketing Science, vol. 27, No. 2, pp. 184-206, Academy of Marketing Science (1999), 23 pages.

Belch et al., "Psychophysiological and Cognitive Response to Sex in Advertising," Advances in Consumer Research, vol. 9, pp. 424-427, (1982), 6 pages.

Blakeslee, "If You Have a 'Buy Button' in Your Brain, What Pushes It?" The New York Times, www.nytimes.com, (Oct. 19, 2004), 3 pages.

Braeutigam, "Neuroeconomics-From neural systems to economic behaviour," Brain Research Bulletin, vol. 67, pp. 355-360, Elsevier, (2005), 6 pages.

Buschman, et al., "Top-Down versus Bottom-Up Control of Attention in the Prefrontal and Posterior Parietal Cortices," Science, vol. 315, www.sciencemag.org/cgi/content/full/315/5820/1860, American Association for the Advancement of Science, (2007), 4 pages.

Canolty, et al., "High Gamma Power Is Phase-Locked to Theta Oscillations in Human Neocortex," Science, vol. 313, www.sciencemag.org, (Sep. 15, 2006), 3 pages.

Canolty, et al., "The functional role of cross-frequency coupling," Trends in Cognitive Sciences, Elsevier, (Nov. 2010) 11 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

D'Esposito, "From cognitive to neural models of working memory," Philosophical Transitions of the Royal Society B, doi: 10.1098/rstb.2007.2086, (Mar. 30, 2007), 12 pages.

Davidson, et al., "The functional neuroanatomy of emotion and affective style," TRENDS in Cognitive Sciences, vol. 3, No. 1, (Jan. 1999), 11 pages.

Desmet, "Measuring Emotions: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

(56) References Cited

OTHER PUBLICATIONS

EEG Protocols, "Protocols for EEG Recording," retrieved from the Internet on Aug. 23, 2011, http://www.q-metrx.com/EEGrecordingProtocols.pdf, (Nov. 13, 2007), 3 pages.

Fogelson, et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.

Fries, Pascal, "A mechanism for cognitive dynamics: neuronal communication through neuronal coherence," Trends in Cognitive Sciences, vol. 9, No. 10, pp. 474-480, Elsevier B.V. www.sciencedirect.com, (Oct. 2005), 7 pages.

Fuster, Joaquin M., "Cortex and Memory: Emergence of a New Paradigm," Journal of Cognitive Neuroscience, vol. 21, No. 11, pp. 2047-2072, Massachusetts Institute of Technology, (Nov. 2009), 26 pages.

Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, (2005), 11 pages.

Haq, Amber, "This Is Your Brain on Advertising," Business Week, Market Research, (Oct. 8, 2007), 4 pages.

Hartikainen et al., Manuscript Draft of "Emotionally arousing stimuli compete with attention to left hemispace," NeuroReport, (Sep. 8, 2007), 26 pages.

Hazlett et al., "Emotional Response to Television Commercials: Facial EMG vs. Self-Report," Journal of Advertising Research, (Apr. 1999), 17 pages.

Keren et al., "Saccadic spike potentials in gamma-band EEG: Characterization, detection and suppression," NeuroImage, http://dx.doi:10.1016/j.neuroimage.2009.10.057, (Oct. 2009), 16 pages.

Kishiyama et al., "Novelty Enhancements in Memory Are Dependent on Lateral Prefrontal Cortex," The Journal of Neuroscience, pp. 8114-8118, Society for Neuroscience (Jun. 24, 2009), 5 pages.

Knight, Robert T., "Contribution of human hippocampal region to novelty detection," Nature, vol. 383, www.nature.com, (Sep. 19, 1996), 4 pages.

Knight, Robert T., "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.

Lee et al., "What is 'neuromarketing'? A discussion and agenda for future research," International Journal of Psychophysiology, vol. 63, pp. 199-204, Elsevier (2006), 6 pages.

Lekakos, George, "Personalized Advertising Services Through Hybrid Recommendation Methods: The Case of Digital Interactive Television," Department of Informatics, Cyprus University, (2004), 11 pages.

Lewis et al., "Market Researchers make Increasing use of Brain Imaging," ACNR, vol. 5, No. 3, pp. 36-37, (Jul./Aug. 2005), 2 pages.

Lui et al., "Marketing Strategies in Virtual Worlds," The Data Base for Advances in Information Systems, vol. 38, No. 4, pp. 77-80, (Nov. 2007), 4 pages.

Makeig et al., "Dynamic Brain Sources of Visual Evoked Responses," Science, vol. 295, www.sciencemag.org, (Jan. 25, 2002), 5 pages.

Makeig et al., "Mining event-related brain dynamics," TRENDS in Cognitive Sciences, vol. 8, No. 5, (May 2004), www.sciencedirect.com, 7 pages.

Miltner et al., "Coherence of gamma-band EEG activity as a basis for associative learning," Nature, vol. 397, www.nature.com, (Feb. 4, 1999), 3 pages.

Moran et al. "Peak frequency in the theta and alpha bands correlates with human working memory capacity," frontiers in Human Neuroscience, vol. 4, Article 200, www.frontiersin.org, (Nov. 11, 2010), 12 pages.

Neurofocus—Neuroscientific Analysis for Audience Engagement, accessed on Jan. 8, 2010 at http://web.archive.org/web/20080621114525/www.neurofocus.com /BrandImage.htm, (2008), 2 pages.

Nielsen, "Neuroinformatics in Functional Neuroimaging," Informatics and Mathematical Modeling, Technical University of Denmark, (Aug. 30, 2002), 241 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Simon-Thomas et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.

Sutherland, Max, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.

Swick et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.

Voytek et al., "Shifts in gamma phase-amplitude coupling frequency from theta to alpha over posterior cortex during visual tasks," Frontiers in Human Neuroscience, doi: 10.3389/fnhum.2010.00191, (Oct. 19, 2010), 9 pages.

Wang, Xiao-Jing, "Neurophysiological and Computational Principles of Cortical Rhythms in Cognition," Physiol Rev 90: pp. 1195-1268, American Physiological Society, www.prv.org, (2010), 75 pages.

Woodman et al., "Serial Deployment of Attention During Visual Search," Journal of Experimental Psychology: Human Perception and Performance, vol. 29, No. 1, pp. 121-138, American Physiological Association (2003), 18 pages.

Yuval-Greenberg et al., "Transient Induced Gamma-Bands Response in EEG as a Manifestation of Miniature Saccades," Neuron, vol. 58, pp. 429-441, Elsevier Inc. (May 8, 2008), 13 pages.

Ziegenfuss, Jennifer S., "Neuromarketing: Advertising Ethical & Medical Technology," The Brownstone Journal, vol. XII, Boston University, pp. 69-73, (May 2005), 9 pages.

Zyga, Lisa, "A Baseball Cap That Can Read Your Mind," PhysOrg.com, located at www.physorg.com/news130152277.html, (May 16, 2008), 11 pages.

Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.

Clifford, Stephanie, "Billboards That Look Back," The New York Times, NYTimes.com, available at http://www.nytimes.com/2008/05/31/business/media/31billboard.html, (May 31, 2008), 4 pages.

Bimler et al., "Categorical perception of facial expressions of emotion: Evidence from multidimensional scaling," Cognition and Emotion, vol. 15(5), pp. 633-658 (Sep. 2001), 26 pages.

De Gelder et al., "Categorical Perception of Facial Expressions: Categories and their Internal Structure," Cognition and Emotion, vol. 11(1), pp. 1-23 (1997), 23 pages.

Newell et al., "Categorical perception of familiar objects," Cognition, vol. 85, Issue 2, pp. 113-143 (Sep. 2002), 31 pages.

Padgett et al., "Categorical Perception in Facial Emotion Classification," In Proceedings of the 18th Annual Conference of the Cognitive Science Society, pp. 249-253 (1996), 5 pages.

Klimesch, Wolfgang, "EEG alpha and theta oscillations reflect cognitive and memory performance a review and analysis," Brain Research Reviews, vol. 29, 169-195, (1999), 27 pages.

Krakow et al., "Methodology: EEG-correlated fMRI," Functional Imaging in the Epilepsies, (Lippincott Williams & Wilkins, 2000), 17 pages.

Krugman, "Brain Wave Measures of Media Involvement," Journal of Advertising Research vol. 11, No. 1, pp. 3-9 (Feb. 1971), 7 pages.

(56) References Cited

OTHER PUBLICATIONS

Palva et al., "Phase Synchrony Among Neuronal Oscillations in the Human Cortex," Journal of Neuroscience 25 (2005), 3962-3972, 11 pages.

Lachaux et al., "Measuring Phase Synchrony in Brain Signals," Human Brain Mapping 8 (1999), 194-208, 15 pages.

Zhang, P., "Will You Use Animation on Your Web Pages?" Doing Business on the Internet: Opportunities and Pitfalls, C. Romm and F. Sudweeks (eds.), Spring-Verlag (1999), 17 pages.

Coan et al., "Voluntary Facial Expression and Hemispheric Asymmetry Over the Frontal Cortex," Psycophysiology (Nov. 2001), 912-924, 14 pages.

Duchowski, "A Breadth-First Survey of Eye-tracking Applications," Beahavior Research Methods, Instruments, and Computers (Nov. 2002), 455-470, 16 pages.

Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.

Rothschild et al., "Predicting Memory for Components of TV Commercials from EEG," Journal of Consumer Research (Mar. 1990), p. 472-478, 8 pages.

Beaver, John D., et al., "Individual Differences in Reward Drive Predict Neural Responses to Images of Food", J. of Neuroscience, (May 10, 2006), 5160-5166, 7 pages.

Shandlen et al., "A Computational Analysis of the Relationship between Neuronal and Behavioral Responses to Visual Motion", The Journal of Neuroscience, (Feb. 15, 1996) 1486-1510, 25 pages.

Cassanello et al., "Neuronal Responses to Moving Targets in Monkey Frontal Eye Fields", J Neurophysiol (Sep. 2008), 1544-1556, 16 pages.

Bandari et al., "The Pulse of News in Social Media: Forecasting Popularity," ICWSM, Feb. 2012, 9 pages.

Rodriguez et al., "Social Networks for News Media Distribution," STB-RL: Digital Library Research and Prototyping, Los Alamos National Laboratory, 2006, 6 pages.

\* cited by examiner

SYSTEM AND METHOD FOR GATHERING AND ANALYZING BIOMETRIC USER FEEDBACK FOR USE IN SOCIAL MEDIA AND ADVERTISING APPLICATIONS

CROSS REFERENCE TO RELATED APPLICATIONS

This application claims priority to U.S. Provisional Patent Application No. 61/603,528, filed Feb. 27, 2012, the entire disclosure of which is incorporated by reference herein.

FIELD OF THE INVENTION

The present invention relates to systems and methods for measuring biologically and behaviorally based responses to social media, locations, or experiences and providing instant and continuous feedback in response thereto. In addition, the system and methods of the invention are capable of monitoring stress levels and well-being. The system and methods of the invention may be implemented using a cloud-based infrastructure for remote monitoring.

BACKGROUND OF THE INVENTION

There are many different kinds of audio, visual and audio-visual presentations and activities that people are exposed to every day. These presentations serve as sensory experiences that stimulate our senses and are known to result in biologically based responses that can be measured electronically and mechanically (for example, heart rate, respiration rate, blood pressure, and skin conductance).

Likewise, people now have the ability to provide instant and continuous feedback in response to various social media such as pictures, websites, and the like. Such feedback can be provided on computers, tablets, smart phones, and other devices that access the internet. For example, "like" is a way to give positive feedback or to connect with things a person is interested in on the popular social media site Facebook®. In particular, the "like" button on Facebook® is a button a user may click on after looking at most content on Facebook®, which is then reported in newsfeeds to "friends". Websites unrelated to Facebook® may also use a "like" button that enables a website visitor to click on the button to let his/her friends know that they like the site. For example, after clicking on the website's "like" button, a pop-up will request login to Facebook® (or sign-up if not already a member) and a post on the user's Facebook® page will let his/her friends know that he/she likes the site. When used on a mobile device, such as a smart phone, the "like" button is merely an integrated hardware "Facebook®" button on the phone that does nothing more than take the user to Facebook® when the button is pressed.

Similarly, the "Pin It" button on a computer or mobile device allows users to grab images and videos from around the web and add them to an on-line pinboards created by the users. Other users can view the pinboards, comment, and "re-pin".

Capabilities have also been introduced to allow people to use mobile devices to interact with their environment. For example, location-based social networking websites allow users to "check-in" at venues using a mobile website, text messaging, or a device-specific application by selecting from a list of venues the application locates nearby. The location is based on GPS hardware in the mobile device or the network location provided by the application. Each check-in awards the user points or other types of rewards.

Even with these advances in technology, the ability to measure and evaluate the user experience, effectiveness, and the usability of social media, locations, or experiences has been limited. In fact, current methodologies for measuring or evaluating user experience, effectiveness, and usability of websites and other interactive internet and software media has thus far been limited to traditional self-report, i.e., relying on the user to use the "like" button and to accurately reflect his/her actual response to the social media, which may be subject to error, bias, or low compliance.

Thus, a need in the art exists for a system and method that integrates passive biometric sensors into smart phones or other portable devices to collaborate with or eliminate the "like" button and replace it with a continuous stream of emotional responses across all experiences. A need also exists in the art for a biometrically enabled suite of applications that are built into smart phones, tablets, and other social media enabled devices to determine when a user unconsciously likes (or dislikes) their current experience, e.g., a web page, "app", song, video, location, or other experience, and also to remotely monitor the user's stress levels and well-being.

SUMMARY OF THE INVENTION

The present invention is related to a system and method that integrates passive biometric sensors into smart phones or other portable devices to collaborate with or eliminate the "like" button and replace it with a continuous stream of emotional responses across all experiences. In one embodiment of the invention, biometric responses may be automatically detected using physiological signal measurement, via an explicit button on the mobile device, or via a continuous biometric data collector. In one embodiment, the biometric data collector is associated with the mobile device, such as a case that incorporates sensors to collect data from the hands of the user.

In another embodiment of the invention, the response may be automatically associated with specific content stimuli, not only in the mobile phone, but also in the surrounding environment of the consumer using a specialized content-associating system (predicting/associating by "proximity" of the response to the variety of content/activities).

In yet another embodiment, the system and method of the invention provides content recommendations by transforming emotional responses to music, video, and other content into more effective and pervasive recommendations. In still another embodiment, the system and method of the invention enhances advertisement targeting by combining biometric sensing and location-based data based on anticipated emotional responses. In yet another embodiment, the system and method of the invention add emotional intelligence to social networks by generating a complex dataset of interests from which users can share and connect with friends. In still another embodiment, the system and method of the invention continually performs background searches based on emotional reactions to any activity in order to push more relevant information to consumers.

The present invention is also directed to a system for determining the emotional response of a user to social media including: a plurality of biometric sensors in a first device operable to measure a plurality of biometric parameters for a user of the first device when exposed to a social media application, marketing or advertising applications, or a combination thereof; a computer system operable to receive data representative of the plurality of biometric parameters, wherein the computer system further includes a memory capable of storing the data, wherein the system is capable of determining an emotional response of the user, identifying the causation of the emotional response, and delivering the emotional response and the causation to a listening application for appropriate action.

In one embodiment, the plurality of biometric parameters include at least two of galvanic skin response, heart response, motion, skin temperature, breathing, EEG, EMG, pupil dilation, eye tracking, facial expressions, or a combination thereof. In another embodiment, the first device includes a device capable of accessing a social media application, a marketing or advertising application, or a combination thereof. For example, the first device may be selected from the group consisting of mobile devices, tablets, laptops, desktops, goggles, watches, and combinations thereof.

In another embodiment, the first device further includes image acquisition functionality, and wherein the image acquisition functionality includes static photographs, videos, or a combination thereof. For example, the image acquisition functionality may include at least one camera, and wherein the at least one camera is capable of acquiring a plurality of images including images in the user's view, images of the user, or a combination thereof. The system may also be capable of image recognition of the images in the user's view. In yet another embodiment, the system may be capable of processing facial recognition using the images, videos, or a combination thereof of the user.

The present invention is also directed to a system for determining the emotional state of a user to social media including: a first device capable of accessing a social media application marketing or advertising applications, or a combination thereof; a second device including at least one biometric sensor operatively connected to the first device, wherein the at least one biometric sensor is operable to measure at least one biometric parameter for a user of the first device when exposed to social media; a computer system operable to receive data representative of the at least one biometric parameter, wherein the computer system further includes a memory capable of storing the data, wherein the system is capable of determining an emotional response of the user to the social media, and wherein the system is capable of delivering the emotional response to a targeted application for appropriate action.

In one embodiment, the at least one biometric parameter includes galvanic skin response, heart response, motion, skin temperature, breathing, EEG, EMG, pupil dilation, eye tracking, facial recognition, or a combination thereof. In another embodiment, the second device includes at least two biometric sensors. In still another embodiment, the at least two biometric sensors are operable to measure at least two biometric parameters selected from the group consisting of galvanic skin response, heart response, motion, skin temperature, breathing, EEG, EMG, pupil dilation, eye tracking, facial recognition, and combinations thereof.

The first device may further include image acquisition functionality. In one embodiment, the image acquisition functionality includes at least one camera, and wherein the at least one camera is capable of acquiring a plurality of images including at least one image in the user's view, at least one image of the user, or a combination thereof. The system may be capable of image recognition of the at least one image in the user's view, facial recognition of the at least one images of the user, or a combination thereof.

In another embodiment, the system may be capable of collecting motion data to determine activity level, direction, or a combination thereof. In yet another embodiment, the system is capable of determining a current activity of the user. In still another embodiment, the system may be capable of feeding the current activity and the emotional state to listening applications, wherein the listening applications reside on the device or on a central server. The listening application may be capable of providing tailored content to the user based on the emotional state and current activity. The listening application may also be capable of processing feeds of the emotional state and current activity for social media.

BRIEF DESCRIPTION OF THE FIGURES

Further features and advantages of the invention can be ascertained from the following detailed description that is provided in connection with the drawing(s) described below.

DETAILED DESCRIPTION OF THE INVENTION

Figure 1:
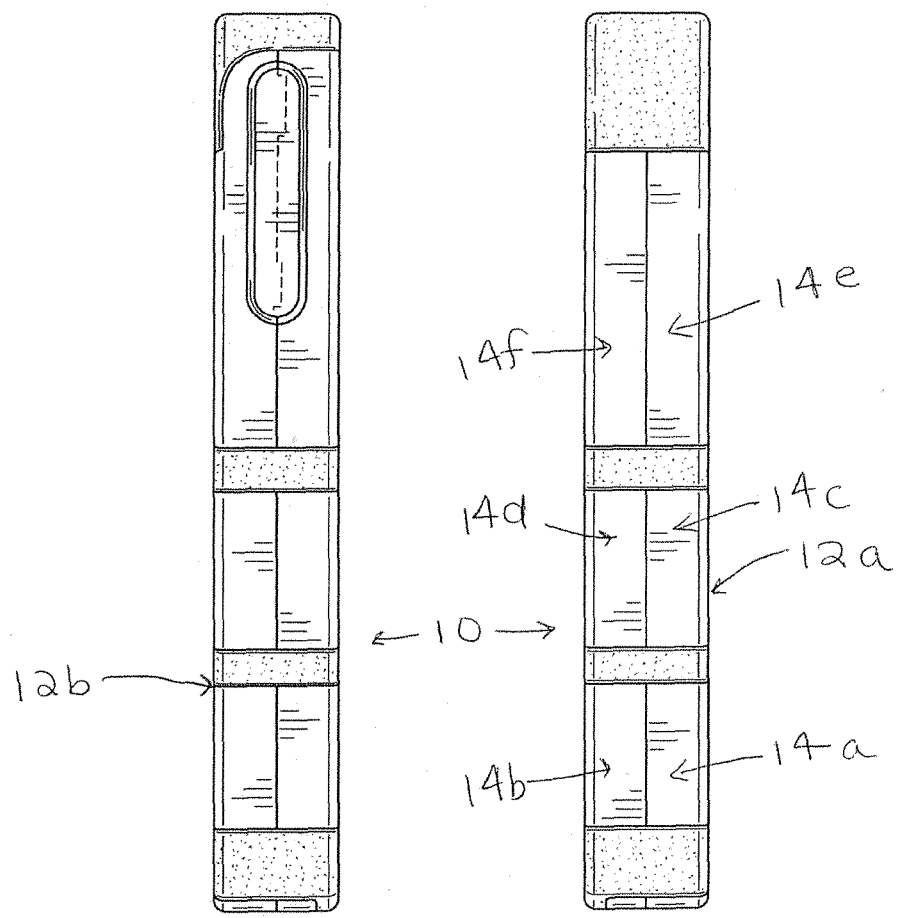
FIG. 1 is a side view of a suitable biometric data collector for mobile devices according to an embodiment of the invention.

The present invention is directed to asocial media interface that will execute social media functions when pressed, rather than simply open a social media application. In particular, the system and method of the invention will accomplish at least one of the following:
 (a) determine a user's current activities;
 (b) among the current activities, select the one that is the most likely activity that the user wants to take action on;
 (c) undertake a specific defined social media action; and/or
 (d) serve related information to the user based on the social media action taken.

The result of the system and method of the invention is the creation of a continuous stream of social media data that provides a richer and more usable experience than active and discreet "liking" in existing social media applications.

In addition to measuring relevant emotional responses, the system and method of the invention is also capable of computing overall stress and other vital signals of the user to establish the general stress levels and well-being of the user. In one embodiment of the invention, the system and method of the invention is implemented at least in part with a cloud-based infrastructure that allows remote monitoring of the user's vital signs and biological signatures for well-being and derived parameters thereof. This information can then be combined with the user's location and activities over time to further define the drivers of well-being (and the opposite thereof (i.e., stress)). In this aspect of the invention, the system may also include the creation of web/mobile interfaces for sharing the user's well-being and derived parameters thereof with the user's specified social network, specified contacts or groups, as well as with designated family or designated health care providers.

In one embodiment, the system and method of the invention incorporates at least one affinity button or software application on a mobile device, such as a smart phone, a tablet, or other device that is capable of accessing a social media application. For example, to determine the user's current activities, when the affinity button is pressed or the application is started, the device will use some or all software and sensors available to determine the possible set of activities the user may be engaged in. This includes, but is not limited to, all or a subset of the following:

(1) The current application being used;
(2) The user's current location to determine what is located at that location;
(3) Images and/or video within the user's view and/or images of the user;
(4) Neighboring devices; and/or
(5) Motion data.

In particular, with regard to (1), a software layer may determine if the mobile device is currently running any applications and which application is in the foreground. For example, in one embodiment, the process/application using the most central processing unit (cpu) in the current time (e.g., past 15 seconds, past 60 seconds, or another predetermined time interval) may be the application in the foreground. In this aspect, the following steps may be performed:

(a) Determination of the application currently running (to the degree the OS allows);
(b) If the foreground application is a web browser, determining at least (i) the current URL, (ii) text characters and image tags on the current page, and (iii) text characters and images in view (accounting for any scroll in the pages, and the like);
(c) If the foreground activity is a photo viewer (either native or embedded in another app), determining the subject, time, date, and the like by gathering and analyzing the metadata in the photo and leveraging image recognition capabilities (either developed specifically for this application or commercially available);
(d) If music, videos, or eBooks are being played or viewed on the mobile device, return all accessible information about the content;
(e) If the audio/video is external to the mobile device, allowing the user to record a "snapshot" and capture an affinity to the snapshot such that the system may then go back to the internet to extract metadata for the audio/video content (using tools/apps that already exist for audio/video);
(f) If a map or navigation application, determine which location is being researched; and/or
(g) If other applications, gather and analyze any data the application allows the operating system to access. For example, application vendors will likely be encouraged to use software hooks which the social media button can use to determine the exact activity within an application is being accessed.

With regard to (2), the mobile device may use the cellular networks, accessible Wi-Fi and/or GPS to (a) determine the user's current location and (b) search to determine what activities may be available at that location. In particular, the determination of the available activities may favor businesses, parks, addresses in the users' address book, tourist spots, or other activities identifiable through the internet. For example, in one embodiment, locations at the GPS coordinates that have the most details online or in point-of-interest databases will be favored.

With regard to (3), the mobile device may acquire a plurality of snapshots and/or video upon a button press or, if programmed, automatically. The plurality of snapshots and/or video may include images in view of the user and images of the user. In one embodiment, the plurality of images/videos may then be run through image recognition software created for the application to determine the image in view (e.g., a product, location, logo, person, etc.). In another embodiment, the plurality of images/videos may then be run through existing software (such as Google Goggles or the like) to determine the image in view (e.g., a product, location, logo, person, etc.). Facial detection software may also be used to determine which specific facial-emotion is being expressed for the activity.

With regard to (4), the mobile device may use Bluetooth to determine whether there are any known devices in the area. In one embodiment, pressing the affinity button near a second user with the same capability on his/her mobile device will identify that device and add it to the identifiable device list as well as the second user's information to the primary user's phone's contact database.

With regard to (5), motion data may be obtained to determine whether the mobile device is manipulated in such a way to indicate that the user is attempting to capture an image. If such action is determined, the image recognition process described with respect to (3) will be given preference in the activity determination. Motion data may also be used to determine whether the mobile device is in "heavy" motion or "light" motion. In particular, if the mobile device is determined to be in "heavy" motion, i.e., walking briskly, running, and the like, preference will be given to activities requiring more action. Conversely, "light" movement or no movement may indicate less active current activities, such as web browsing or movie watching. Accordingly, preference will be given to less active activities. Motion data may also be used to determine the direction of the mobile device such that, in conjunction with (2) above, an appropriate landmark may be identified. In one embodiment, the motion data may be obtained using at least one of an accelerometer, a magnometer, a gyroscope, or a combination thereof.

With regard to (1)-(5), the system and method of the invention then predict the current activity using a set of likely rules. In particular, the system may use a set of likely rules to determine the most likely relevant activity in the mobile device and/or surrounding environment by monitoring the increases in "recent" time window in the (1) the cpu usage, (2) the memory usage, (3) the decibel (volume) usage, (3) the images being viewed, (4) the online social activity, (5) the online web page interactions, (6) the online or web game interactions, and other similar categories.

More specifically, in one embodiment of the invention, the system and method of the invention will also be capable of selecting a likely activity from the collected set. In particular, machine learning will be employed to determine which potential activity is the activity meant to be tagged via social media. Examples of machine learning in accordance with the present invention include, but are not limited to, the following:

(a) A training period. When the user initiates the affinity button push, a list of possible primary activities is provided. The user will then select the intended activity. Over time, this trains the system to prioritize the selected activity based on prior use. For example, if the user tends to select the song being played, the system will prioritize music as the likely item of interest. Alternatively, a more passive training model may be followed. In this aspect, the system would suggest a single likely activity and the user would respond whether this was correct or for the system to try again. The system would then suggest an alternative (or an open field for the user to suggest an alternative) and the process would continue. Through machine learning, the system would create appropriate weighting to possible activities of interest to hone its suggestions.

(b) Background service. In another embodiment, the software may run as a background service, regularly querying the device to determine the current activity through all of, or a subset of, the activities covered in the previous section. When the user then expressly activates this software, it will first compare the current state to the previous state(s) to determine what has changed and then determine the desired activity of focus by combining the state change information with (1) any previous training, if it exists (2) compare to previous items the user has taken action on to determine if it fits with the user profile and (3) prioritize actions taken on the cell phone (browser, apps, new music, video or other content being played) over environmental processes like Bluetooth and GPS.

(c) Recent items. Instead of querying multiple sensors, in one embodiment, the machine training involves a determination of the most recently opened item on the mobile device and acts upon it. If no suitable application has been opened or changed, it will then look to the other sensors and activities.

(d) Prioritization. Machine training may involve the prioritization of activities. For example, in one embodiment, activities taken on the mobile device over any environmental activities (GPS, Bluetooth, external audio) have first priority, camera action has second priority, GPS and audio recordings have third priority, and Bluetooth and other sensors have fourth priority. As would be understood by one of ordinary skill in the art, these priorities may be appropriately altered based on any additional information on the activity of the user to create a prioritization system for "guesstimating" the activity of a user. The "guesstimation" may then be associated with extracted biological/emotional/facial responses based on all and sundry information available on the usage of the background/foreground apps, in-view objects and current events pertaining to the user (at his/her location).

The above-described forms of machine learning may be used independently or together.

Once an activity is determined, the system will then take the desired social media action(s). Suitable social media actions include, but are not limited to:

(a) Execution of a function defined in the system that may or may not be editable by the user. For example, the function may be a Facebook® "like", a Twitter post, a Facebook® update, a Pinterest® addition, a Foursquare check-in, a Google+, or any other standard action within social media interfaces (whether it be directly actions in current platforms, future platforms, or a separate platform specifically created for this functionality);

(b) Execution of a custom action such as a "dislike", a "yum" for food related items, or other actions directly related to the current activity; and/or (c) Execution of more standard functions like a bookmark, a favorite, a pin, or a web search.

In one embodiment, (c) may include a web search based on any or all of the current possible activities. For example, a user is at a sports bar in Location A watching a Soda 1 commercial featuring Singer X with a couple of friends on his/her mobile device. During the commercial, the user holds up the phone to a Picture Z on the wall and presses the affinity button. The system will go through its normal process of determining the liked action, but will also (i) perform a web search on each item returning a search results page split into sections showing information on Location A, Picture Z, the sports bar, their friends, Singer Z and Soda 1 and (ii) flag all of these items in a social media list stored on the mobile device for future search and reference. In other words, (c) may be a form of social media in a natural environment bookmark.

Once these actions are taken, the information can be stored in a form of customer relationship management (CRM) database enabling advertisers to target messages to these users based on items they have flagged using this application. Over time, advertising within the app or across the operating system will become increasingly more directed at the user.

Biometrics may also be integrated into or associated with the device in order to ascertain the emotional state of the phone user. Biometrics include, but are not limited to galvanic skin response (GSR) to measure emotional arousal, heart response (approach/avoid), motion to determine activity level), skin temperature, breathing, EEG, EMG, pupil dilation, eye tracking, and facial recognition. The sensor(s) used to collect the biometrics may be integrated into the hardware platform through additional sensors.

Figure 2:
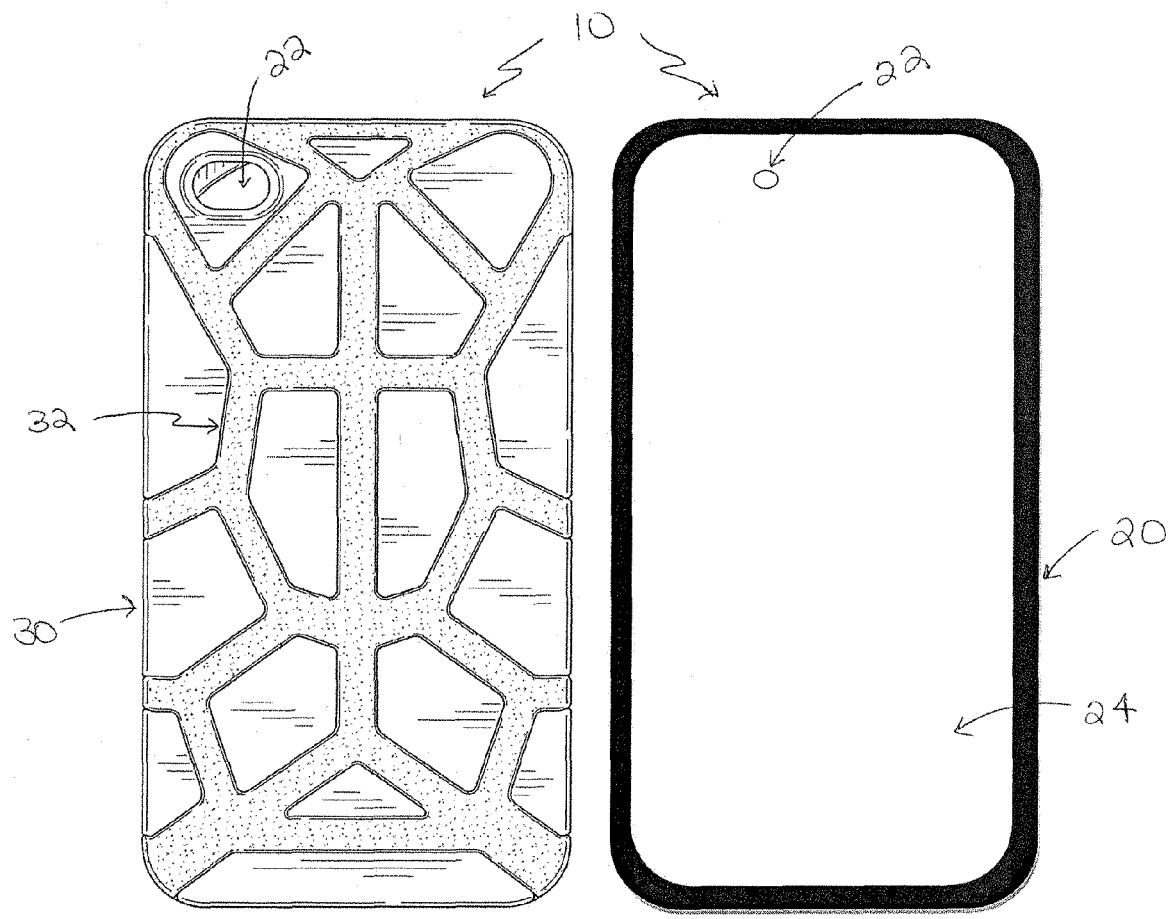
FIG. 2 is a front and rear view of the suitable biometric data collector for mobile devices shown in FIG. 1.

In one embodiment, the biometric data collection is performed through a sensor-array case on the back, sides, and/or front of the existing mobile device. For example, as shown in FIGS. 1 and 2, the case 10 has sides 12a and 12b, a front 30, a back 20, and a top and bottom (not shown). The case 10 does not cover the display of the mobile device, as indicated by void 24. The biometrics discussed above may be captured via a plurality of sensors 14 and/or 32. A subset of the biometrics, i.e., heart response, breathing, pupil dilation, eye tracking, and facial recognition, may be captured via sensors 14, built-in camera 22, and/or sensors 32. While FIG. 1 shows sensors 14 only on one side, i.e., side 12a, side 12b may also be equipped with one or more sensors.

Figure 3A:
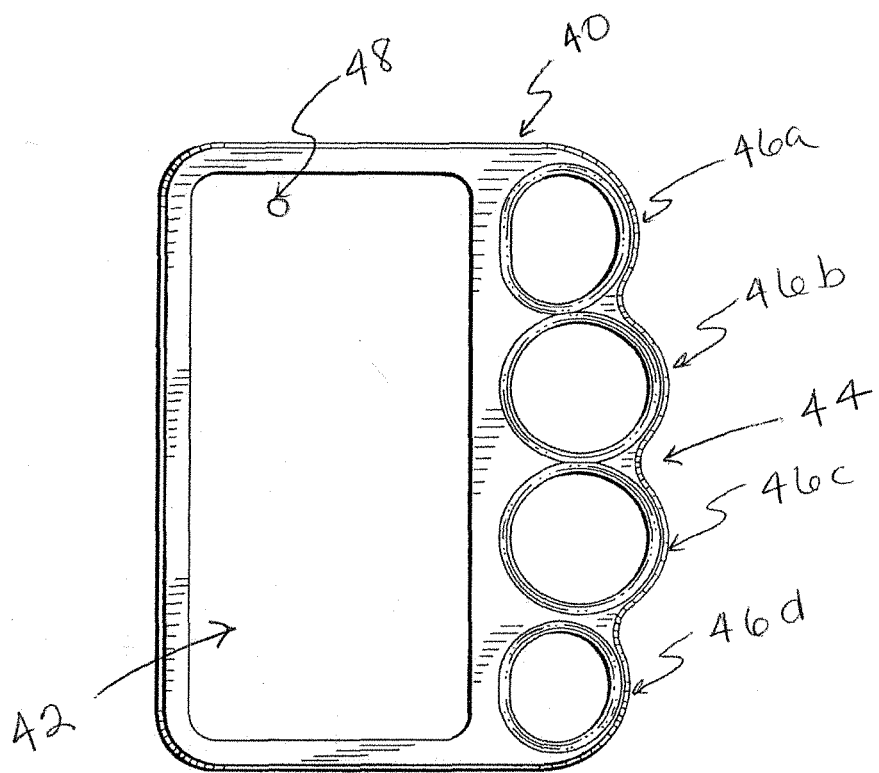
FIGS. 3A and 3B are front views of a suitable biometric data collector for mobile devices according to another embodiment of the invention.
Figure 3B:
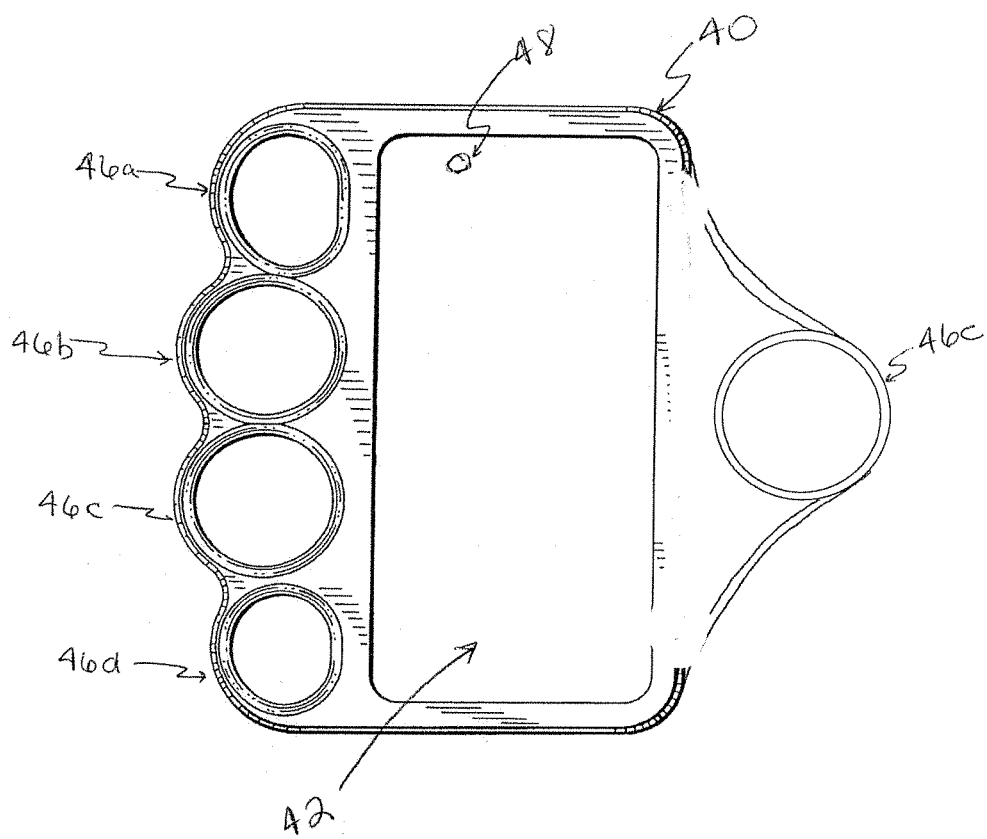

FIG. 3A shows another embodiment of a biometric data collector for use with a mobile device. In particular, the case 40 has an opening for the mobile device 42 and the built-in camera 48. At least one sensor for biometric data collection is incorporated into at least one of the finger holes 46a-d. While FIG. 3A shows four finger holes 46a-d, one of ordinary skill in the art would appreciate that more or less finger holes may be used in the case design so as to facilitate biometric data collection. For example, as shown the case 40 may incorporate five finger holes 46a-e such that the thumb hole 46e is on an opposite side of case 40 than finger holes 46a-d. In addition, as with the case shown and described in FIGS. 1-2, a subset of the biometrics, i.e., heart response, breathing, pupil dilation, eye tracking, and facial recognition, may be captured via the sensors in finger holes 46, the built-in camera 42, and/or sensors built into the back of case 40 (not shown). Similarly, one of ordinary skill in the art would appreciate that, while FIGS. 3A-B illustrate a case 40 intended for right-handed users, the case could be modified to accommodate left-handed users by changing the side(s) on which the finger holes 46*a*-*d* (and optionally 46*e*) reside.

Figure 4A:
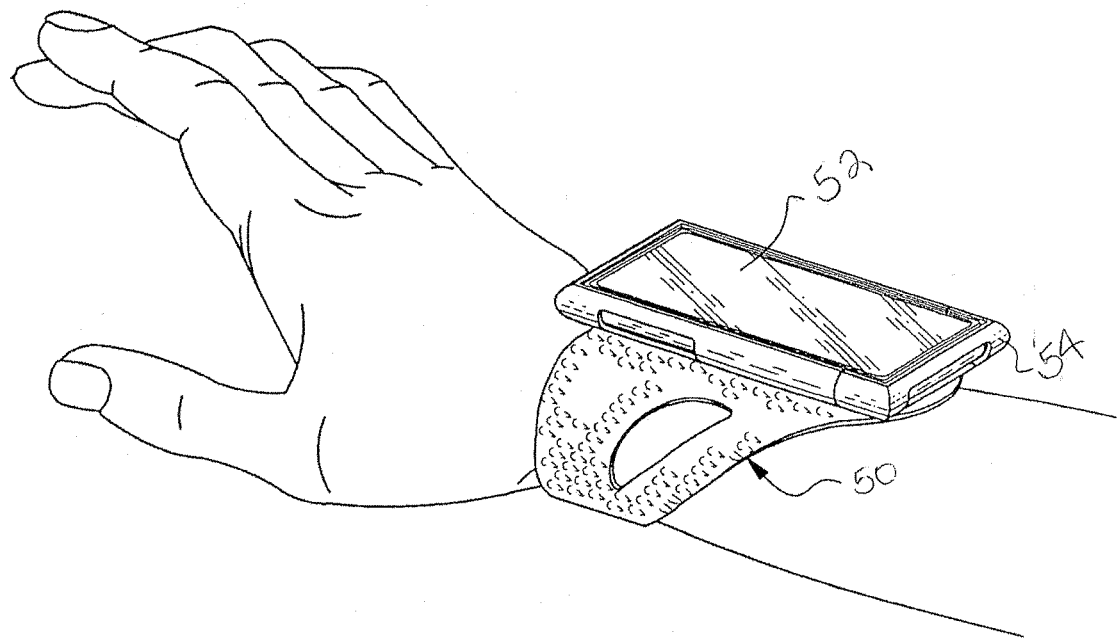
FIGS. 4A and 4B are a perspective views illustrating a suitable biometric data collector in position on a mobile device user's wrist according to an embodiment of the invention.
Figure 4B:
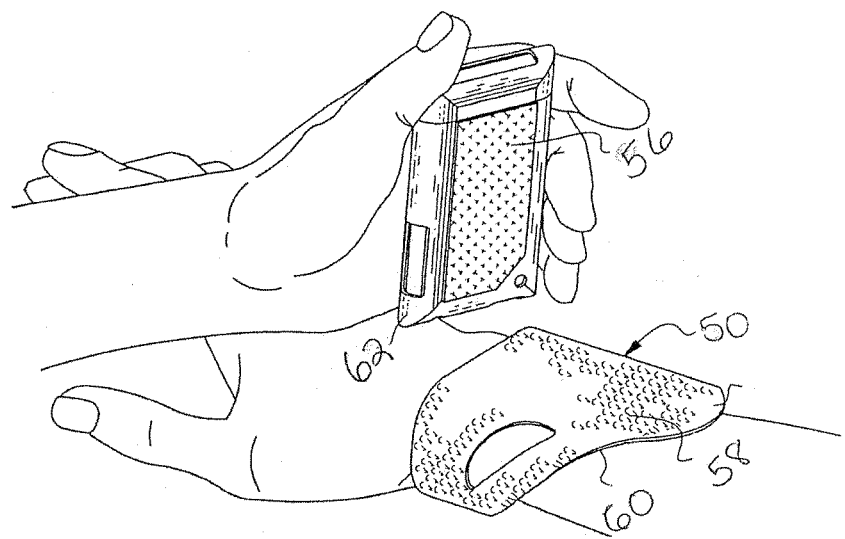
Figure 5:
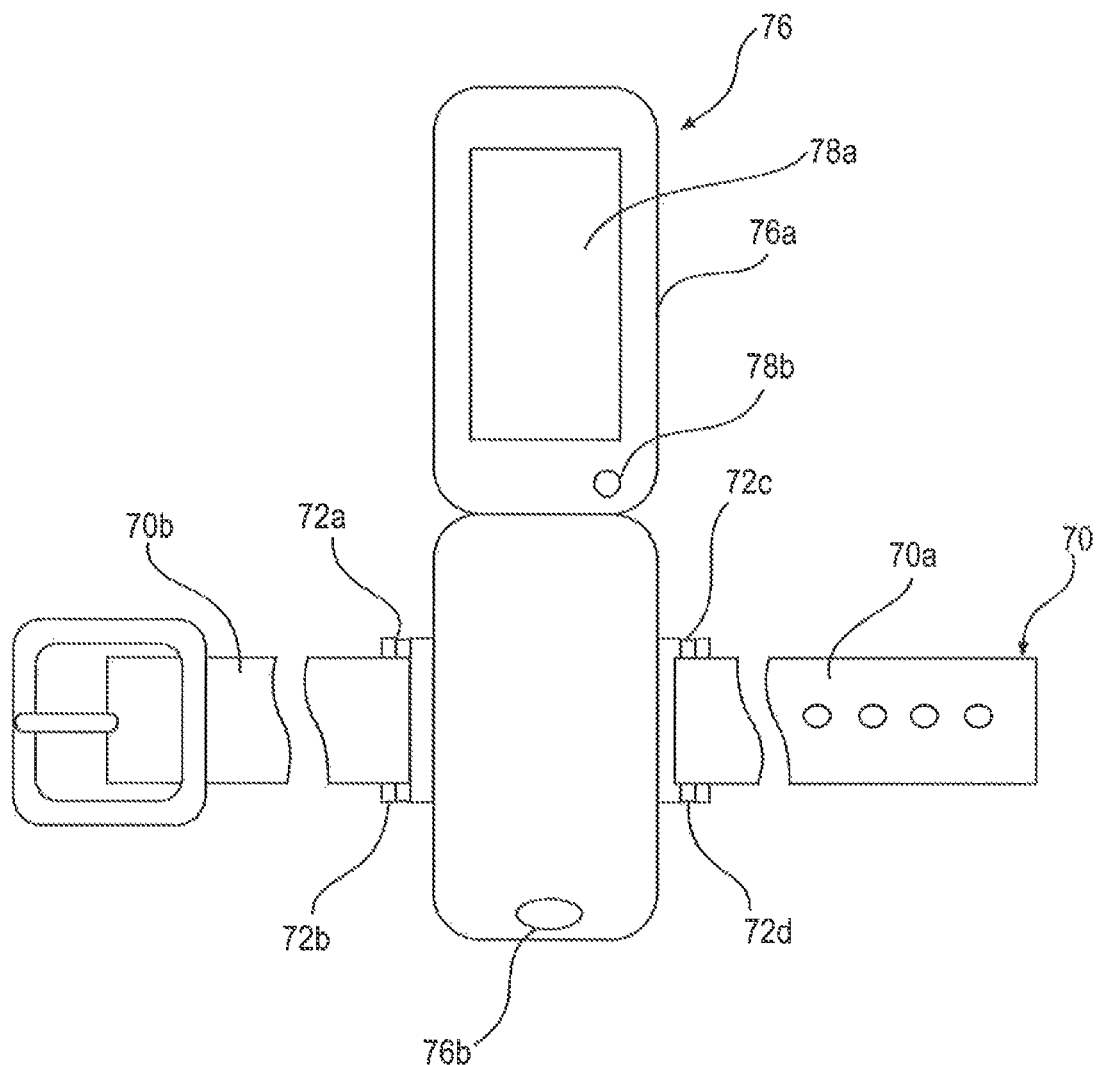
FIG. 5 is a front view illustrating a suitable biometric data collector according to an embodiment of the invention.

In another embodiment, the biometric data collector is incorporated into a wrist or arm band, such as those shown in FIGS. 4A-B and FIG. 5. In particular, a wrist band 50 may utilize a hook and loop fastener system 58, 56 to attach the mobile device 52 or its case 54. At least one sensor 60 may be incorporated into the wrist band 50. In one embodiment, a plurality of sensors may be incorporated into the wrist band. The wrist band 50 may also include an emitter that transmits the data to a wireless or wired receiver in the mobile device 52. Similarly, arm band 70 with straps 70*a* and 70*b* include at least one sensor 72 for biometric data collection (four sensors 72*a*-*d* are shown here as a non-limiting example of the plurality of sensors that may be used in accordance with the invention). The front 76*a* and back 76*b* of case 76 may house the mobile device. The case 76 may have an opening 78*a* for the mobile device display and an opening 78*b* for a camera built in to the mobile device. As with the previous embodiments, the arm band may include an emitter to transmit the biometric data to a wired or wireless receiver in the mobile device.

Figure 6:
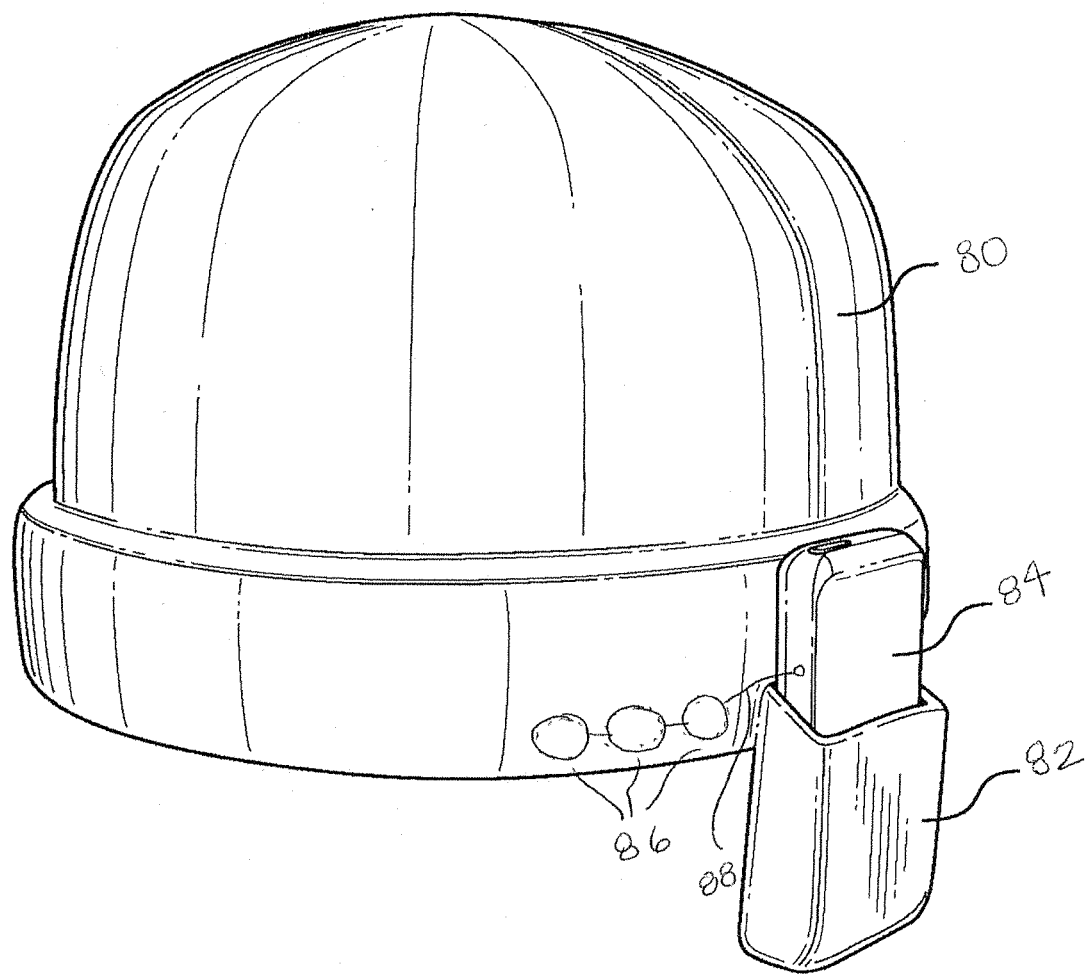
FIG. 6 is a perspective view of a biometric data collector with a mobile device in place according to an embodiment of the invention.

In yet another embodiment, the biometric data collector is incorporated into headgear, such as the hat illustrated in FIG. 6. Headgear of any style may be incorporated into this embodiment of the present invention. In this instance, a winter hat is used with a pocket portion 82 attached such that in use at least one sensor (shown here as 86) in the hat 80 will properly be aligned with the user's temple. The sensor(s) is in direct communication with the mobile device 84 via a wired connection 88. However, as one of ordinary skill in the art would appreciate, the wired connection may be substituted for a wireless connection such that the biometric data collected via the one or more sensors 86 will be received by the mobile device 84.

Figure 7:
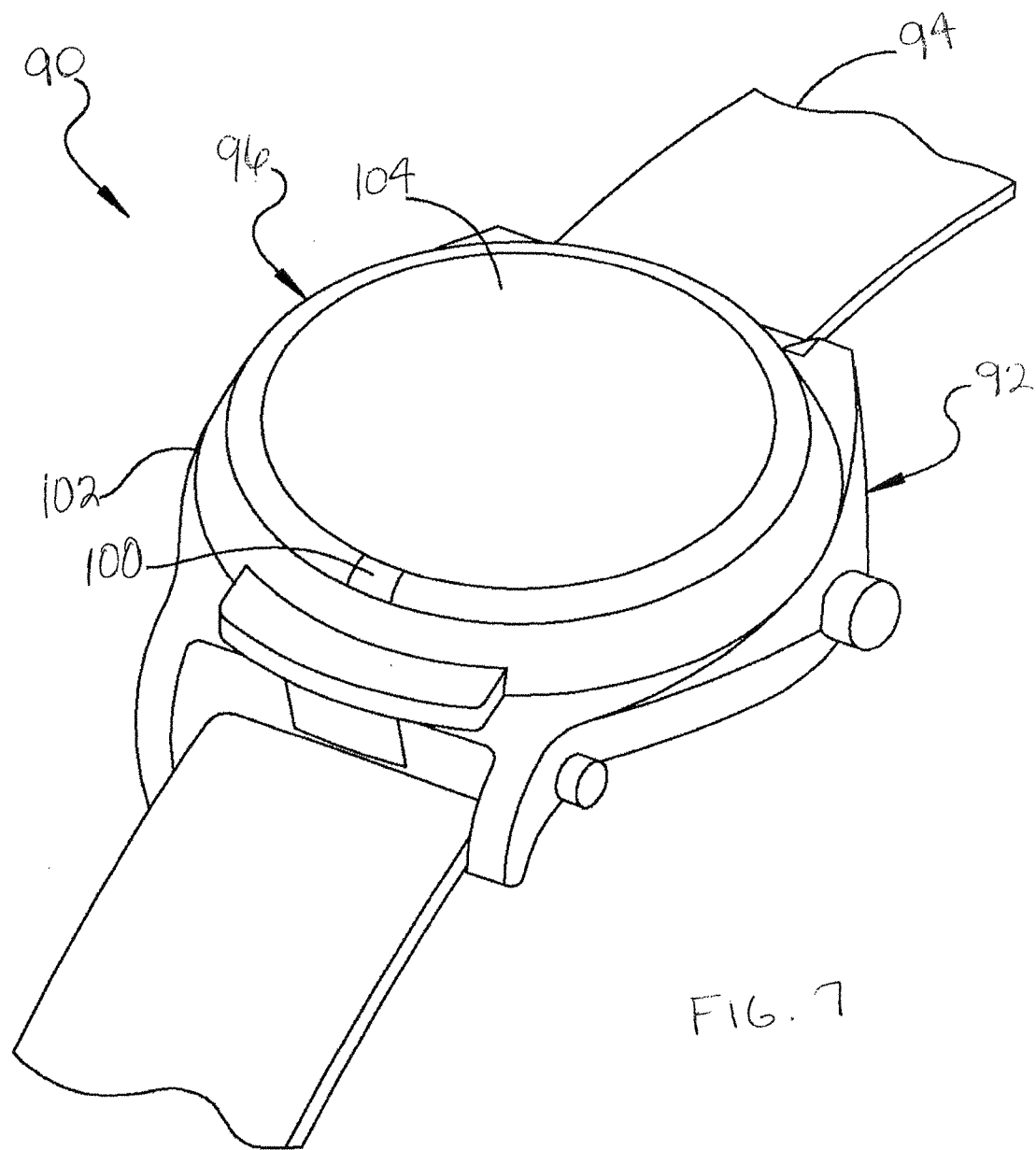
FIG. 7 is a perspective view of a suitable biometric data collector according to an embodiment of the invention.

In still another embodiment, the biometric data collector may be incorporated into a smart watch, as generally shown in FIG. 7. For example, a smart watch 90 may include a base 92, a wristband 94 coupled to the base 92, a flip up portion 96, a hinge 98 coupled to the base 92 and the flip up portion 96, and a camera 100. The base 92 may include at least one housing 102 that includes a processor, a wireless transceiver, and at least one sensor (not shown) coupled to the housing 102. The sensors and wireless transceiver may be coupled to the housing and in communication with the processor. In one embodiment, a tactile user interface in communication with the processor and coupled to the housing is accessible via flip up portion 96 but viewable through display 104. The wireless transceiver can provide a connection to a wireless network. As with the previous embodiments, the at least one sensor in the housing 102 is capable of collecting biometric data.

Figure 8:
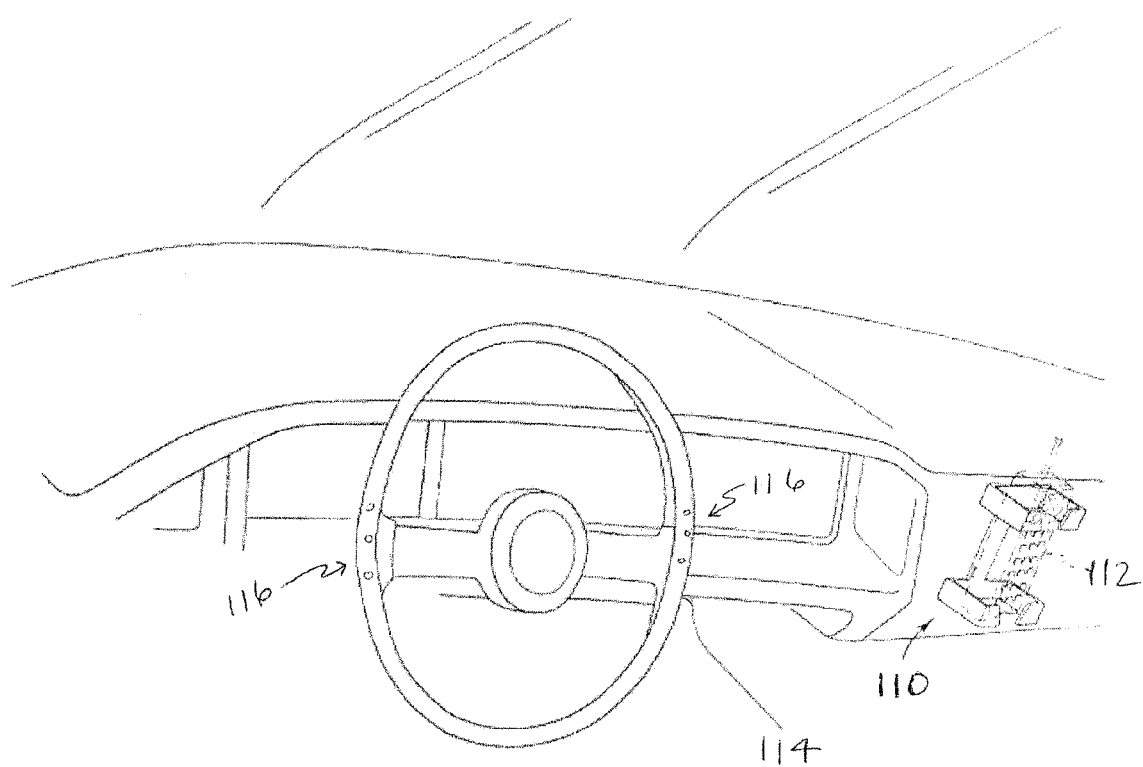
FIG. 8 is a perspective view of a suitable biometric data collector according to an embodiment of the invention.

In another embodiment, the biometric data collector may be incorporated into a steering wheel of a vehicle. For example, as shown in FIG. 8, a mobile device 112 may be housed in holder 110. Holder 110 may be connected to sensors 116 via a wired or wireless connection such that biometric data may be collected.

Furthermore, while additional sensors may be added directly through integrated hardware, a subset of the sensors may require an external monitoring device (due to sensor needs on other parts of the body). In this aspect of the invention, suitable sensors for collecting EEG and EMG include, but are not limited to, an armband, a pair of glasses, a watch, and similar sensors. In one embodiment, all of the remaining sensors are built into a secondary device. Some, such as a breathing sensor, may work more effectively in a secondary device that communicates with the device of the invention.

In an alternative embodiment, the system of the invention incorporates a device that is not a handheld device. In other words, instead of incorporating the sensors into a mobile phone, the device used is a pair of glasses with attached sensors to the scalp, the forehead, or the like, which are designed with all of the required sensors and equipment as most handheld technology devices. In one aspect, the glasses include a visible screen and sensors (e.g., sensors to the central-parietal regions of the head for EEG, to the forehead, chin or neck for the skin-conductance and to the neck for heart-rate, or other optimal locations on the face/neck of a person for these biological signals), that may have otherwise required a secondary device. The collection of biometric data distinguishes the glasses described in this embodiment from conventional eye tracking goggles.

The biometric data thus collected is intended to determine the emotional state of the user. This emotional state may then be used to activate the social media function with limited button presses. Thus, in one aspect of the invention, the affinity button or application may be used in conjunction with the biometric data. In this aspect, the mobile device (via sensors incorporated directly into the mobile device, into the biometric data collector holding the mobile device, and/or other external secondary devices) is capable of gathering biometric data to determine current physical and emotional state. Affinity buttons may be selected to perform the following steps:

1) ascertain the current activity the user is engaged in as described in the previous section;
2) determine the degree of acceptance of the current activity (i.e., whether the current activity is liked or disliked); and/or
3) execute the actions described in the previous section.

The affinity buttons exist on the mobile device solely for training the system on the user's biometric profile. In particular, as a particular affinity button is pressed, a biometric snapshot is taken of the user to determine the emotional state. The snapshot may then be stored as a biometric fingerprint associated with both the self-described state (positive or negative) and the current activity. As the user builds this dataset, the system begins to suggest content (e.g., music, video, books), products, locations, and the like for future biometric states (without actual button presses). Indeed, at a predetermined stage, the button presses may be completely removed. For example, if every time a user presses the positive affinity button when their heart rate and GSR spike above a threshold while listening to Elvis music, when the user has similar future spikes, the system may recommend listening to similar music.

In addition, the affinity buttons assist in training the system/device. For example, the user presses the particular affinity buttons to train the system that biometric patterns are associated with liking and disliking. In one embodiment of the invention, the system will be able to continuously monitor the user's biometrics. When the system senses a biometric profile/signature pattern matching "like" or "dislike", the system automatically takes the associated social media action, which would then execute the series of steps listed in the previous function on a continuous basis without the user ever having to press a button. The buttons or applications may be removed or disabled after the system is adequately trained.

In an alternate embodiment of the system, the training algorithm occurs completely outside the biometric device (using a simulated environment), or through predictions of valence and arousal, such as through the methods described in U.S. Pat. No. 8,296,172 and U.S. Patent Publication Nos. 2010/0211439 and 2010/0004977, the entire disclosures of which are incorporated herein by reference.

Alternatively, the system may be a device that has no affinity buttons and only relies on the biometric sensors to accomplish the end goal. In this aspect, no additional training is necessary (existing techniques as described in U.S. Pat. No. 8,296,172 and U.S. Patent Publication Nos. 2010/0211439 and 2010/0004977 for predicting valence, arousal, and engagement, and resonance may be used). In this embodiment, the system continuously determines emotional/biometric state such that whenever a specific emotional state of interest, such as an approach or avoid response, is identified, the series of activities previously described are followed, i.e., determining current activity and taking desired social media actions.

Other embodiments are within the scope and spirit of the invention. For example, functions described above can be implemented and/or automated using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. A system comprising:
    a first sensor to determine an activity of a mobile device;
    a second sensor to determine an environment surrounding the mobile device;
    a third sensor to measure biometric parameters associated with a user of the mobile device; and
    a processor to execute instructions to:
        determine an emotional response of the user based on the biometric parameters;
        associate the activity related to the mobile device and the environment surrounding the mobile device with the emotional response of the user;
        detect a social media action performed by the user in a social media application;
        correlate the social media action with the emotional response, the activity of the mobile device, and the environment surrounding the mobile device; and
        create and store a record of the correlation of the social media action with the emotional response, the activity of the mobile device, and the environment surrounding the mobile device;
        automatically perform the social media action a subsequent time in accordance with the record based on (1) a subsequent determination of the emotional response and (2) a subsequent determination of one or more of (a) the activity of the mobile device or (b) the environment surrounding the mobile device, wherein the social media action is performed in accordance with a priority schedule that prioritizes association of the subsequent emotional response and the subsequent activity of the mobile device over the association of the subsequent emotional response and the subsequent environment.

2. The system of claim 1, wherein the mobile device is configured to access a marketing or advertising application, or a combination thereof.

3. The system of claim 1, wherein the mobile device is at least one of a smart phone, a tablet, a laptop, a desktop, goggles, and a watch.

4. The system of claim 1, including an image acquisition device capable of acquiring at least one of an image or a video representing the user's view, the user, or a combination thereof.

5. The system of claim 4, wherein the processor is to perform image recognition on at least one of the image or the video representing the user's view.

6. The system of claim 4, wherein the processor is to perform facial recognition on at least one of the image and the video.

7. A system comprising:
    a first sensor to determine social media being accessed by a mobile device in a social media application;
    a second sensor to determine an environment surrounding the mobile device;
    a third sensor to measure a biometric parameter associated with a user of the mobile device;
    a memory including machine executable instructions; and
    a processor to execute the instructions to:
        determine an emotional response of the user based on the biometric parameter;
        associate the social media accessed by the user and the environment surrounding the mobile device with the emotional response;
        detect a social media action performed by the user in response to the social media;
        correlate the emotional response to the social media action performed by the user, the social media accessed by the user, and the environment surrounding the mobile device;
        create and store a record of the correlation of the social media action with the emotional response, the social media accessed by the user, and the environment surrounding the mobile device; and
        automatically perform the social media action a subsequent time in accordance with the record based on (1) a subsequent determination of the emotional response and (2) a subsequent determination of one or more of (a) the social media accessed by the user or (b) the environment surrounding the mobile device, wherein the social media action is performed in accordance with a priority schedule that prioritizes association of the subsequent emotional response and the subsequent accessing of the social media over association of the subsequent emotional response and the subsequent environment.

8. The system of claim 7, wherein the third sensor includes at least two biometric sensors.

9. The system of claim 8, wherein the at least two biometric sensors are structured to measure at least two of galvanic skin response, heart response, motion, skin temperature, breathing, EEG, EMG, pupil dilation, eye tracking, facial recognition, or a combination thereof.

10. The system of claim 9, further including an image acquisition device to acquire an image in the user's view, an image of the user, or a combination thereof.

11. The system of claim 10, wherein the processor is to perform image recognition on the image in the user's view, the image of the user, or the combination thereof.

12. The system of claim 7, wherein the processor is to collect motion data to determine activity level, direction, or a combination thereof.

13. The system of claim 7, wherein the processor is to determine a current activity of the user.

14. The system of claim 13, wherein the processor is to transmit the current activity and the emotional response to an application residing on the mobile device or on a central server.

15. The system of claim 7, wherein the processor is provide tailored content to the user based on the emotional response.

16. The system of claim 7, wherein the processor is to modify a social media feed based on the emotional response.

17. The system of claim 1, wherein the third sensor is to monitor vital signs and biological signatures for well-being and share the vital signs and biological signatures with a health care provider.

18. The system of claim 1, wherein the processor is to determine if a second mobile device is in proximity to the mobile device and to add contact information relating to the second mobile device to the mobile device in response to selection of an affinity input by the user.

19. The system of claim 1, wherein the processor is to associate a signature of biometric parameters to the activity of the user.

20. The system of claim 19, wherein the processor is to suggest a further activity to the user based on the emotional response matching the signature.

21. The system of claim 19, wherein the processor is to determine the further activity based on the signature.

22. The system of claim 1, wherein the biometric parameters include at least one of: galvanic skin response, heart response, motion, skin temperature, breathing, EEG, EMG, pupil dilation, eye tracking, or facial expressions.

23. The system of claim 1, wherein the processor is to execute machine learning to identify the activity related to the mobile device, to execute the machine learning the processor is to at least one of:
- analyze user input from a training period,
- use a background service to monitor activities on the mobile device,
- use a most recently opened item on the mobile device, or
- prioritize activities based on respective types of the activities.

* * * * *